US006485746B1

(12) United States Patent
Campbell et al.

(10) Patent No.: US 6,485,746 B1
(45) Date of Patent: Nov. 26, 2002

(54) CONTROLLED-RELEASE SEDATIVE-HYPNOTIC COMPOSITIONS AND METHODS RELATED THERETO

(75) Inventors: D. Bruce Campbell; W. Jay Thiele, both of San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/649,343

(22) Filed: Aug. 28, 2000

Related U.S. Application Data
(60) Provisional application No. 60/240,930, filed on Aug. 25, 2000.

(51) Int. Cl.[7] .............................. A61K 9/14; A61K 9/22
(52) U.S. Cl. .................... 424/468; 424/489; 514/772.3; 514/774; 514/778; 514/782; 514/783; 514/781; 514/785; 514/923
(58) Field of Search ................................. 424/457, 461, 424/462, 463, 476, 480, 481, 482, 489, 468, 465, 490, 494, 495, 496, 497

(56) References Cited

U.S. PATENT DOCUMENTS

| 4,382,938 A | 5/1983 | Kaplan et al. .............. 424/256 |
| 4,460,592 A | 7/1984 | Kaplan et al. .............. 424/256 |
| 4,521,422 A | 6/1985 | Dusza et al. ................ 514/258 |
| 4,626,538 A | 12/1986 | Dusza et al. ................ 514/258 |
| 4,654,347 A | 3/1987 | Dusza et al. ................ 514/258 |
| 4,794,185 A | 12/1988 | Rossey et al. .............. 546/121 |
| 4,808,594 A | 2/1989 | George et al. .............. 514/300 |
| 4,847,256 A | 7/1989 | Tseng et al. ................ 514/258 |
| 4,900,836 A | 2/1990 | Tomcufcik et al. ......... 546/279 |
| 4,948,592 A | 8/1990 | Ayer et al. .................. 424/473 |
| 5,538,977 A | 7/1996 | Dusza et al. ................ 514/258 |
| 5,714,607 A | 2/1998 | Padmanathan .............. 544/281 |
| 5,788,987 A | 8/1998 | Busetti et al. .............. 424/480 |
| 5,891,891 A | 4/1999 | Benincasa ................... 514/300 |

FOREIGN PATENT DOCUMENTS

| EP | 1 005 863 A1 | 6/2000 |
| EP | 1 064 937 A1 | 1/2001 |
| WO | WO 98/13029 | 4/1998 |
| WO | WO99/57101 | 11/1999 |
| WO | WO 00/33835 | 6/2000 |
| WO | WO01/00181 | 1/2001 |

OTHER PUBLICATIONS

Foster, "Developments in CNS Drugs II: Drugs of Tomorrow," SMi Conference, London, UK, May 11–12th, 1999.

Primary Examiner—James M. Spear
(74) Attorney, Agent, or Firm—Seed Intellectual Property Law Group PLLC

(57) ABSTRACT

Controlled-release formulations providing a "pulsed" plasma profile of a sedative-hypnotic compound having a particularly short half-life are provided. The formulation contains a sedative-hypnotic compound or precursor thereof that is metabolized to generate a sedative-hypnotic compound in vivo, wherein the compound has a mean plasma half life ranging from 0.1 to 2 hours; and at least one release retardant such that, following administration of the formulation to a patient, the patient has specified pulsed plasma profile for the sedative-hypnotic compound as disclosed herein. In a preferred embodiment, the sedative-hypnotic compound is NBI-34060.

35 Claims, 9 Drawing Sheets

NBI-34060
Double Rapid Peak Absorption

CONTROLLED-RELEASE SEDATIVE-HYPNOTIC COMPOSITIONS AND METHODS RELATED THERETO

CROSS REFERENCE TO RELATED APPLICATION

This application claims benefit of U.S. application No. Ser. 09/384,448 filed Aug. 26, 1999, which application was converted to U.S. Provisional Application No. 60/240,930 by petition filed Aug. 25, 2000.

TECHNICAL FIELD

The present invention relates generally to compositions and methods for the treatment of insomnia and related conditions. The invention is more particularly related to controlled-release sedative-hypnotic compositions with particularly short half-lives, and methods for using such compositions to promote rapid sleep onset and sleep maintenance.

BACKGROUND OF THE INVENTION

Many physiological functions are characterized by diurnal rhythms, in which levels of circulating hormones, catecholamines and other compounds fluctuate during the day and/or night. Certain medical disorders, such as insomnia, are associated with abnormalities in these rhythms. The time, within a 24 hour period, of administration of drugs for the prevention and treatment of such disorders can be a critical factor in determining efficacy of the therapy.

The term "insomnia" refers to the perception of inadequate or non-restful sleep by a patient. Insomnia is a frequent complaint, reported by 32% of the adult population surveyed in the Los Angeles area (Bixler et al, *Amer. Journal of Psychiatry* 136:1257–1262, 1979), and 13% of the population surveyed in San Marino, Italy (Lugaresi et al., *Psychiatric Annals* 17:446–453, 1987). Fully 45% of the surveyed adult population of Alachua County, Florida, reported trouble getting to sleep or staying asleep (Karacan et al., *Social Science and Medicine* 10:239–244, 1976). The prevalence of insomnia has also been shown to be related to the age and sex of the individuals, being higher in older individuals and in females.

Early treatments for insomnia commonly employed central nervous system (CNS) depressants such as barbiturates. These compounds are typically long acting (on the order of 8–50 hours) due to long terminal half-lives, and have a well-known spectrum of side effects, including lethargy, confusion, depression and next day hangover effects. In addition, chronic use has been associated with a high potential for addiction involving both physical and psychological dependence.

During the 1980's, the pharmaceutical treatment of insomnia shifted away from barbiturates and other CNS depressants toward the benzodiazepine class of sedative-hypnotic agents. This class of compounds produces a calming effect that results in a sleep-like state in humans and animals, with a greater safety margin than prior hypnotics. The therapeutic actions of benzodiazepines are believed to be mediated by binding to a specific receptor on benzodiazepine GABA complexes in the brain. As a result of this binding, synaptic transmission is altered at neurons containing the benzodiazepine GABA complex. The clinical usefulness of different benzodiazepine hypnotics relates largely to their pharmacokinetic differences with regard to this binding and, in particular, to the half-lives of the parent compound and its active metabolites. However, many benzodiazepines possess side effects that limit their usefulness in certain patient populations. These problems include synergy with other CNS depressants (especially alcohol), the development of tolerance upon repeat dosing, rebound insomnia following discontinuation of dosing, hangover effects the next day and impairment of psychomotor performance and memory. Next day sleepiness and memory impairment, which can include amnesia for events occurring prior to and after drug administration, is of particular concern in the elderly whose cognitive functions may already be impaired by the aging process.

More recent treatments for insomnia have used non-benzodiazepine compounds, which show an improved side effect profile over the benzodiazepine class of sedative-hypnotics. The first of these agents to be approved by the United States Food and Drug Administration (FDA) for marketing in the United States was Ambien (zolpidem), which is based on the imidazopyridine backbone (see U.S. Pat. Nos. 4,382,938 and 4,460,592). In addition to Ambien, another compound known as Sonata (zaleplon), which is a pyrazolopyrimidine-based compound (see U.S. Pat. No. 4,626,538), was recently approved by the FDA. Other non-benzodiazepine compounds and/or methods for making or using the same have also been reported (see, e.g., U.S. Pat. Nos. 4,794,185, 4,808,594, 4,847,256, 5,714,607, 4,654,347; 5,538,977, 5,891,891). Attempts have also been disclosed to provide controlled-release dosage forms, particularly in the context of zolpidem and salts thereof (see WO 00/33835 and EP 1 005 863 A1).

Accordingly, there is a need in the art for sedative-hypnotic compositions that induce and maintain sleep as single dose nocturnal formulations, but without the side effects associated with the longer acting hypnotics. The present invention fulfills this need and further provides other related advantages.

SUMMARY OF THE INVENTION

Briefly stated, the present invention provides compositions and methods for promoting sleep. Within one aspect, the present invention provides a controlled-release formulation, comprising (a) a sedative-hypnotic compound, or a precursor thereof that is metabolized to generate a sedative-hypnotic compound in vivo, and (b) at least one release retardant such that, upon administration of the formulation to a patient, the patient has a "pulsed" plasma profile of the sedative-hypnotic compound. As used herein, a "pulsed" plasma profile means that, following administration of the sedative-hypnotic formulation the patient has in the following order:

(i) a time to a first maximum plasma concentration ($Tmax_1$) of the sedative-hypnotic compound ranging from 0.1 to 2 hours following administration;

(ii) a time to a minimum plasma concentration (Tmin) of the sedative-hypnotic compound ranging from 2 to 4 hours, wherein the plasma concentration of the sedative-hypnotic compound at Tmin is less than 80% of the plasma concentration at $Tmax_1$, with the proviso that, in a preferred embodiment, the plasma concentration of the sedative-hypnotic compound at Tmin does not fall below a minimum effective concentration to maintain sleep;

(iii) a time to a second maximum plasma concentration ($Tmax_2$) of the sedative-hypnotic ranging from 3 to 5 hours following administration, wherein the plasma concentration of the sedative-hypnotic compound at Tmax$_2$ is from 80% to 150% of the plasma concentration at Tmax$_1$;

(iv) a plasma concentration of the sedative-hypnotic compound at 6 hours following administration of at least 20% of the plasma concentration at Tmax$_2$; and (v) a plasma concentration of the sedative-hypnotic compound at 8 hours following administration of no more than 20%, and preferably no more than 15%, of the plasma concentration at Tmax$_2$.

Sedative-hypnotic compounds of this invention have particularly short plasma half-lives—that is, less than 2 hours and, more preferably, on the order of about 1 hour. A representative sedative-hypnotic compound is N-methyl-N-(3-{3-[2-thienylcarbonyl]-pyrazolo-[1,5-a]-pyrimidin-7-yl}-phenyl)acetamide (also referred to herein as "NBI-34060"). Representative release retardants include, but are not limited to, hydroxypropylmethyl cellulose, ethyl cellulose, poly (ethylacrylate methylmethacrylate), methacrylic acid copolymer (Type A, Type B, Type C), hydroxypropyl cellulose, carbomer, polyethylene glycol, polyvinylpyrrolidone, gelatin, corn starch, stearyl alcohol, carnuba wax, white wax, glyceryl monostearate, glyceryl distearate, guar gum, xanthan gum and chitosan.

Within further aspects, the present invention provides methods for promoting sleep in a mammal, including a human (collectively referred to herein as a "patient") and particularly in the context of treating chronic insomnia, comprising administering to a patient a controlled-release formulation as described above. Such formulations may, for example, be administered orally, or by any other route that provides a plasma profile as described herein, and have been found to minimize next day residual effects.

These and other aspects of the present invention will become apparent upon reference to the following detailed description and attached drawings.

BRIEF DESCRIPTION OF THE DRAWINGS

FIGS. 2A and 3A illustrate predicted plasma concentrations with a sedative-hypnotic compound having a half-life of 1.3 hours (NBI-34060), while

FIGS. 4A and 5A illustrate the predicted plasma concentrations achieved with a sedative-hypnotic compound outside the scope of this invention, having a half-life of 2.3 hours, while

DETAILED DESCRIPTION OF THE INVENTION

Figure 1:
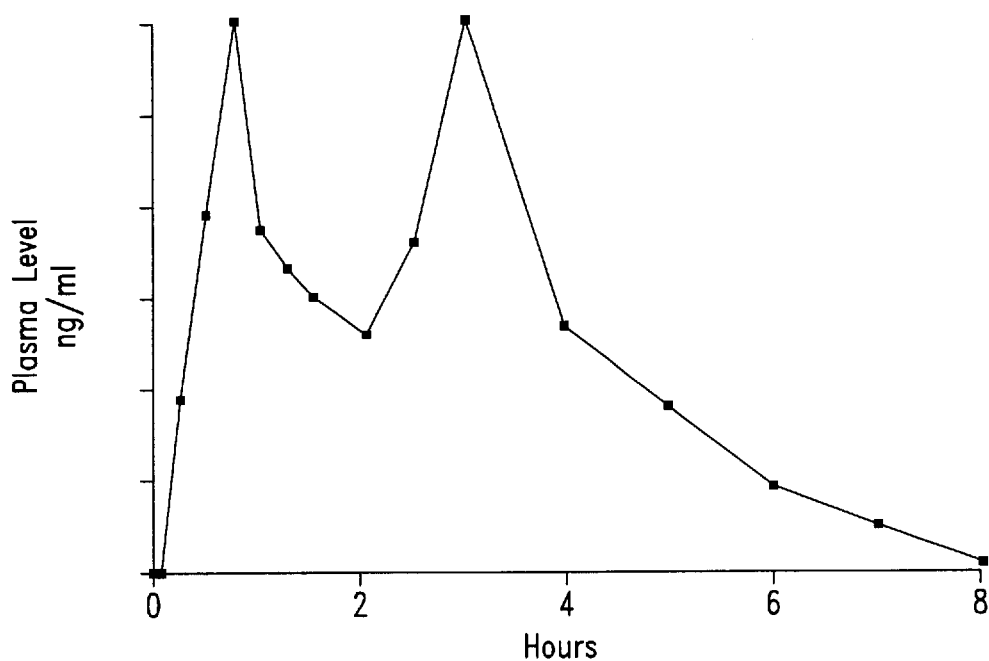
FIG. 1 is a graph illustrating the plasma level over time following administration of a formulation of the present invention that provides for a "pulsed" plasma profile according this invention.

As noted above, the present invention is generally directed to a controlled-release sedative-hypnotic formulation that is characterized by a pulsed release of the active compound(s) over a period of up to eight hours. Formulations as provided herein are particularly useful for administering compounds intended to be active during sleep. As discussed in more detail below, such formulations are preferably orally active, but may be administered by other suitable routes.

The sedative-hypnotic formulations provided herein generally comprise at least one sedative-hypnotic compound having a particularly short plasma half-life of less than 2 hours, and at least one release retardant that controls the rate of compound release following administration to a patient. It has been found, within the context of the present invention, that short acting sedative-hypnotic compounds are particularly useful for promoting rapid sleep onset and/or sleep maintenance through the use of a formulations that generates a "pulsed" release profile as described herein. Such formulations may be used, for example, as single dose nocturnal formulations, which can promote sleep for 7–8 hours, and which do not result in significant next-day residual effects (also referred to as "hangover" effect).

As noted above, short acting sedative-hypnotic compounds are particularly suited for use within the controlled-release formulations described herein. In general, a short-acting sedative-hypnotic compound is a compound that has a detectable sedative effect in any standard assay, with a mean plasma half-life of the compound of less than 2 hours, typically ranging from 0.25 to 1.5 hours, and preferably, in one embodiment, on the order of about 1.3 hours. Such compounds generally show a relationship between hypnotic effect and plasma levels. It will be apparent that a formulation may comprise an active sedative-hypnotic compound or a precursor thereof that is metabolized to generate an active sedative-hypnotic compound in vivo. Both types of formulation are specifically contemplated by the present invention.

The mean plasma half-life of a sedative-hypnotic compound may be determined using well known techniques. Terminal half-life may be determined using standard pharmacokinetic calculations, such as those presented by Rolland and Tozer (*Clinical Pharmacokinetics Concepts and Applications*, 3$^{rd}$. Ed., Chap. 3, 1995). in addition, software is commercially available which performs this calculation, such as the product sold under the tradename "WinNinlin™"(Prof. Ver. 1.5). This software calculates terminal plasma half-life (t1/2) from the following relationship: "t1/2=1n(2)/$\lambda$", wherein "1n(2)" is the natural log of 2 and "$\lambda$" is the first order rate constant associated with the terminal (log-linear) portion of the plasma test compound concentration: time profile. This is estimated by linear regression analysis of the time vs. log concentration of the test compound.

The sedative-hypnotic effect of a compound may be readily established using, for example, standard tests that monitor the effects of a drug on motor activity, muscle relaxation and motor coordination (see, e.g., Beer et al., *CNS Drug Reviews* 3:207–224, 1997; Sanger et al., *Eur. J. Pharmacol.* 313:35–42, 1996, and references cited therein). In general, a sedative-hypnotic compound should have a statistically significant sedative effect within at least one, and preferably all, of the following assays:

(a) assays to detect a reduction in locomotor activity, as described by Sanger et al., *European J Pharmacol.* 313:35–42, 1996 and Beer et al., *CNS Drug Reviews* 3:207–224, 1997;

(b) assays to detect an increase in total sleep time, as determined by electroencephalographic (EEG) measures, as described in Beer et al., *CNS Drug Reviews* 3:207–224, 1997; and (c) assays to detect a reduction in motor coordination, as defined by a reduced latency to remain on a rotating rod and/or a reduction in alertness, or vigilance (both assays as described by Sanger et al., *European J Pharmacol.* 313:35–42, 1996 and Beer et al., *CNS Drug Reviews* 3:207–224, 1997).

A preferred short-acting sedative-hypnotic compound of this invention is N-methyl-N-(3-{3-[2-thienylcarbonyl]-pyrazolo-[1,5-a]-pyrimidin-7-yl }-phenyl)acetamide (NBI-34060). The molecular formula of NBI-34060 is $C_{20}H_{16}N_4O_2S$, and the molecular weight is 376.44 Daltons. NBI-34060 has a half-life of approximately 1.3 hours. The structural formula is shown below:

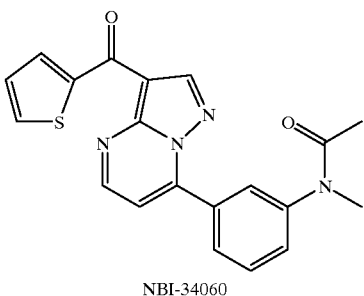

NBI-34060

NBI-34060 occurs as an off-white to yellow, non-free flowing powder with little static charge. The compound is lipid soluble (log D partition coefficient=1.73), and is soluble in water at approximately 20–30 µg/ml with a resulting pH of approximately 8.0. NBI-34060 may be prepared using chemical synthesis techniques known to those skilled in this field.

For example, NBI-34060 may generally be made by the synthetic procedures disclosed in U.S. Pat. Nos. 4,521,422 and 4,900,836 (incorporated herein by reference). These patents, particularly U.S. Pat. No. 4,521,422, disclose a genus encompassing certain aryl and heteroaryl[7-(aryl and heteroaryl)-pyrazolo[1,5-a]pyrimidin-3-yl]methanones. Such compounds may generally be classified as "substituted pyrazolopyrimidines" having the following Genus I:

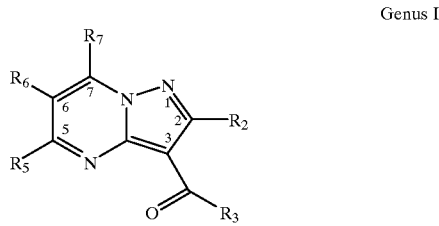

Genus I

In particular, U.S. Pat. No. 4,521,422 discloses that compounds of Genus I may be made by reacting an appropriately substituted pyrazole (a) with an appropriately substituted 3-dimethylamino-2-propen-1-one (b) as represented by the following reaction scheme:

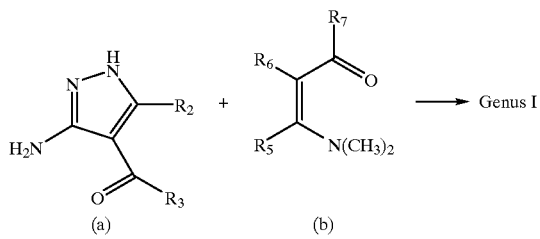

The above reaction will yield NBI-34060 when $R_2$, $R_5$ and $R_6$ are hydrogen, $R_3$ is thienyl, and $R_7$ is 2-(N(Me)COCH_3)-phenyl. Further disclosure directed to the synthesis of NBI-34060 by the above technique is set forth in Example 32.

Another representative sedative-hypnotic compound of this invention is zaleplon (Wyeth-Ayerst), also known as "Sonata", which is a sedative-hypnotic compound recently approved by the FDA as sedative-hypnotic (see U.S. Pat. No. 4,626,538). Sonata has a half-life of approximately 1 hour when administered orally in tablet form. Sonata has about 1/20 the binding specificity of NBI-34060 at the GABA complex.

As discussed in further detail below, NBI-34060 a potent sedative, anxiolytic and anti-convulsant agent, and possesses an improved profile of side effects, as compared to benzodiazepine agents. NBI-34060 shows a reduced tolerance to sedation, a lowered potential for abuse and a reduced tendency to potentiate the deleterious effects of ethanol. In addition, NBI-34060 appears to be substantially devoid of next-day hangover effects and to have a considerably reduced amnesic potential compared to currently marketed sedative-hypnotic agents.

Any of a variety of release retardants may be used within the formulations described herein. The critical feature of a release retardant is the ability to generate a release profile of the sedative-hypnotic compound that provides a "pulsed" plasma level of the compound. As mentioned above, such a release profile yields, in sequential order, the characteristics noted below following administration to a patient:

(i) a time to a first maximum plasma concentration ($Tmax_1$) of the sedative-hypnotic compound ranging from 0.1 to 2 hours following administration;

(ii) a time to a minimum plasma concentration (Tmin) of the sedative-hypnotic compound ranging from 2 to 4 hours, wherein the plasma concentration of the sedative-hypnotic compound at Tmin is less than 80% of the plasma concentration at $Tmax_1$, with the proviso that, in a preferred embodiment, the plasma concentration of the sedative-hypnotic compound at Tmin does not fall below a minimum effective concentration to maintain sleep;

(iii) a time to a second maximum plasma concentration ($Tmax_2$) of the sedative-hypnotic ranging from 3 to 5 hours following administration, wherein the plasma concentration of the sedative-hypnotic compound at $Tmax_2$ is from 80% to 150% of the plasma concentration at $Tmax_1$;

(iv) a plasma concentration of the sedative-hypnotic compound at 6 hours following administration of at least 20% of the plasma concentration at $Tmax_2$; and (v) a plasma concentration of the sedative-hypnotic compound at 8 hours following administration of no more than 20% of the plasma concentration at $Tmax_2$.

As used herein, "Tmax" refers to the "time to maximum plasma concentration" and represents time that elapses between administration of the formulation and a maximal plasma concentration of sedative-hypnotic compound (i.e., a peak in a graph of plasma concentration vs. time). The formulations of this invention display two Tmax values: "$Tmax_1$" is the "time to first maximum plasma concentration", while "$Tmax_2$" is the "time to second maximum plasma concentration. Between $Tmax_1$ and $Tmax_2$, the plasma concentration drops or dips to a value less than that of $Tmax_1$ referred to herein as the "time to minimum plasma concentration" or "Tmin." From Tmin to $Tmax_2$, the plasma concentration increases from the dip concentration to that of $Tmax_2$. This increase in plasma concentration of the sedative-hypnotic compound is believed to be particular beneficial in the context of treating insomnia.

Sleep is controlled by two biological processes, the homeostatic and circadian. The homeostatic drive manifests itself as an increased drive for sleep. This drive for sleep accumulates across the period of wakefulness (typically daytime) and dissipates across the sleep period. The circadian rhythm of sleep-wake shows a biphasic curve with the greatest drive for sleep occurring between midnight and 5AM in the morning, and between 2PM and 4PM in the afternoon. It is believed that major circadian influences are an alerting pulse in the evening and in the morning. It is the interaction of these processes which give rise to the 24-hour sleep schedule. For individuals with a usual sleep period of 11PM to 7AM, sleep onset in the evening occurs primarily as a function of homeostatic drive. After about four hours of sleep (about 3AM) homeostatic drive dissipates significantly and wakefulness begins to intrude into the sleep period. This propensity to increased wakefulness is further increased by the rise in the circadian alerting pulse at about 5AM.

In terms of the pharmacological management of insomnia, two vulnerabilities have been recognized. The first is difficulty initially falling asleep, with the second being reawakening in the middle of the night. The formulations of the present invention address both of these issues by use of a particularly short acting sedative-hypnotic compound which has a single pulse at sleep onset, and a second pulse at the time of the decline in homeostatic processes and rise in the circadian pulse. The increase in plasma concentration from the dip or Tmin value to that of $Tmax_2$ has been found to be particularly beneficial in preventing subsequent awakening of the patient. Much like the initial plasma concentration pulse from time of administration to $Tmax_1$, which results in the patient falling asleep, the pulse from the concentration at Tmin to $Tmax_2$ has been found to be particularly beneficial for sleep maintenance. To this end, it is believed that this increase in plasma concentration is more beneficial than merely maintaining a constant plasma concentration of the sedative-hypnotic compound. For example, by having the plasma concentration dip between $Tmax_1$ and $Tmax_2$ the patient is exposed to a lower overall dosage, thereby decreasing subsequent effects, such as unwanted hangover effect. In addition, a lower plasma concentration at Tmin decreases incidents of nighttime falls and/or amnesia, particularly in the elderly.

In the practice of this invention, the plasma concentration of the sedative-hypnotic at $Tmax_1$ is generally in excess of 5 ng/mL, and normally in the range of 5 ng/mL to 20 ng/mL, typically in the range of 7.5 ng/mL to 15 ng/mL, and preferably in the range of 10 ng/mL to 13 ng/mL. (As disclosed herein, concentration values expressed as "ng/mL" are for NBI-34060.) This plasma concentration is arbitrarily assigned a value of 100% at $Tmax_1$ for comparison purposes to plasma concentrations at subsequent times post-administration. For example, if the plasma concentration at $Tmax_1$ is 10 ng/mL, then 80% of the plasma concentration at $Tmax_1$ means a plasma concentration of 8 ng/mL–that is, 10 ng/mL×0.8 =8 ng/mL. $Tmax_1$ generally ranges in time from 0.1 to 2 hours following administration of the sedative-hypnotic compound, typically from 0.25 to 1 hour and, in one embodiment, is on the order of about 30 minutes and, in another embodiment, on the order of about 1 hour. It is generally desirable to have the time to $Tmax_1$ to be as short as practical such that the patient falls asleep quickly after administration of the sedative-hypnotic.

In the practice of this invention, a "dip" in plasma concentration of the sedative-hypnotic compound occurs at Tmin, which occurs after $Tmax_1$ and prior to $Tmax_2$. This dip results in a plasma concentration of the sedative-hypnotic compound that is generally less than 80%, preferably less than 70%, and typically less than 60% of the plasma concentration at $Tmax_1$. In further embodiments, the concentration at Tmin is less than 50%, or less than 40%, of the plasma concentration at $Tmax_1$. Again, assuming a plasma concentration at $Tmax_1$ of 10 ng/mL, the phrase "less than 80% of the plasma concentration at $Tmax_1$," means that the plasma concentration of the sedative-hypnotic compound is less than 8 ng/mL at Tmin. Similar calculations may be made for the other values set forth above. In a preferred embodiment, the plasma concentration at Tmin does not result in a plasma concentration of the sedative-hypnotic compound less than a nominal level necessary to maintain sleep. Typically, this lower level is in excess of 3 ng/mL, typically in excess of 4 ng/mL, and preferably in excess of 5 ng/mL. Tmin generally ranges from 2 to 4 hours following administration of the sedative-hypnotic compound, and typically from about 2.5 to 3.5 hours and, in one embodiment, is on the order of about 3 hours.

$Tmax_2$ occurs after Tmin, with the increase in plasma concentration from Tmin to $Tmax_2$ representing the increase, as discussed above, of sedative-hypnotic compound to which the patient is exposed. The plasma concentration at $Tmax_2$ is generally in the range of 80% to 150% of the plasma concentration at $Tmax_1$, typically in the range of 90% to 140%, preferably in the range of 100% to 130% and, in one embodiment, is about 100% of the plasma concentration at $Tmax_1$. Again, assuming a plasma concentration at $Tmax_1$ of 10 ng/mL, then the phrase "80% to 150% of the plasma concentration at $Tmax_1$" means a plasma concentration ranging from 8 ng/mL to 15 ng/mL. $Tmax_2$ generally ranges from 3 hours to 5 hours following administration of the sedative-hypnotic compound, typically from 3.5 to 4.5 and, in one embodiment, is on the order of about 4 hours.

At 6 hours after administration of the sedative-hypnotic compound, the plasma concentration is at a level in excess of the amount necessary to maintain sleep. As noted above in the context of the plasma concentration at Tmin, such concentration levels are in excess of 3 ng/mL, typically in excess of 4 ng/mL, and preferably in excess of 5 ng/mL. As a ratio of $Tmax_2$, the plasma concentration at 6 hours is at least 20% of that at $Tmax_2$, typically at least 30%, and, in one embodiment, is on the order of about 40%. The maximum plasma concentration that may be achieved at 6 hours following administration is dependent, at least in part, on the desired plasma concentration of the sedative-hypnotic compound at 8 hours (as discussed below).

At 8 hours after administration, the plasma concentration of the sedative-hypnotic compound is at a level that is not sufficient to maintain sleep, and generally at a level of less than 2 ng/mL. As a function of $Tmax_2$, the plasma concentration at 8 hours is less than 20% of the concentration at $Tmax_2$, and preferably less than 15%. Such a low level of the sedative-hypnotic compound at 8 hours post-administration reduces hangover effect. It should be noted, however, that in order to achieve such low plasma levels at 8 hours post-administration, while still maintaining the pulsed plasma profile disclosed above, the sedative-hypnotic agent must have a particularly short half-life as discussed above.

Suitable release retardants include, but are not limited to, acrylic or other polymers, alkylcelluloses, shellac, zein, hydrogenated vegetable oil, hydrogenated castor oil and mixtures of any of the foregoing. There are numerous release retarding polymers that are commercially available. For example, aqueous dispersions of ethyl cellulose (e.g., Aquacoat™, available from FMC Corp. (Philadelphia, Pa.) or Surelease™, available from Coloron, Inc. (West Point, Pa.) and acrylic resin lacquers (e.g., Eudragit™ dispersions (Rohm Pharma)) are readily available. Other biodegradable, biocompatible polymers, such as ethylene vinyl acetate, polyanhydrides, polyglycolic acid, polyorthoesters, polylactic acid and others known to those of ordinary skill in the art, may also be used. Preferred release retardants include hydroxypropylmethyl cellulose, ethyl cellulose poly (ethylacrylate methylmethacrylate), methacrylic acid copolymer (Type A, Type B, Type C), hydroxypropyl cellulose, carbomer, polyethylene glycol, polyvinylpyrrolidone, gelatin, corn starch, stearyl alcohol, carnuba wax, white wax, glyceryl monostearate, glyceryl distearate, guar gum, xanthan gum and chitosan.

One or more release retardants may be combined with the hypnotic compound, and/or the hypnotic compound (e.g., in combination with a binder and pelletized) may be coated by a material comprising one or more release retardants in a pharmaceutically acceptable solvent, such as water, methanol or ethanol. Such coating may be achieved using standard techniques, such as spraying using any spray equipment known in the art, followed by curing. Methods for using release retardants to obtain a desired release profile are well known in the art and are amply described in the patent and scientific literature (see, e.g., U.S. Pat. Nos. 5,672,360, 5,698,220 and 5,788,987; and EP 908,177 A1). It will be apparent to those of ordinary skill in the art that the physical properties of the coating may be further improved through the use of one or more other components, such as plasticizers, diluents, lubricants, binders, granulating aids, flavorants, glidants and colorants, which may be selected and used according to standard practice (see Handbook of Pharmaceutical Excipients (Eds, A Wade. and P. J. Weiler, second edition, American Pharmaceutical Association, The Pharmaceutical Press, London, 1994); Pharmaceutical Dosage Forms: Tablets, Lieberman, Lachman and Schwartz, ed., $_2$nd edition (Marcel Dekker, Inc.); Remington's Pharmaceutical Sciences, Arthur Osol, ed., pages 1553–1593 (1980)).

Formulations may take any suitable form, including solutions, capsules, tablets, pellets, patches, aerosols and powders. Such formulations may be intended for administration by any known means, including buccal, sublingual, transmembrane, muccusal, transdermal, intranasal, inhalation and rectal administration. Preferably, the formulation is adapted for oral delivery. It will be apparent that other formulation components may be desirable depending on the mode of administration. Formulations used for parenteral, intradermal, subcutaneous or topical application can include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients and/or suitable excipients such as salts, buffers and stabilizers may, but need not, be present within the composition.

To prepare a formulation having a release profile as provided herein, any method that provides for controlled release of the active component with the desired kinetics may be used. For example, one or more drug-rich regions may be deposited within a polymer matrix to provide one or more bursts of sedative release. Additional active component may be incorporated into the matrix to provide for maintenance of plasma levels. Methods for generating drug-rich regions and for incorporating a drug into a matrix are well known, and include methods employing three dimensional printing as described in WO 98/36739.

Controlled release, may also be achieved, for example, using ion exchange microspheres. Such microspheres may be overloaded, resulting in an initial pulse of active component, followed by subsequent release of active component bound to the ion exchange material. It will be apparent that an active component for use within such formulations should be in a salt form, and that the ionic exchange material should be one that, when ionized, contains a suitable charge for interacting with the active component (i.e., a negative charge for use with a positively charged active component, and a positive charge for use with a negatively charged active component). Those of ordinary skill in the art will be readily able to select a suitable ion exchange material. Ion exchange microspheres may be produced using well known procedures, such as spray drying, coacervation and emulsification. The preparation of such formulations is described, for example, in Davis et al., Microsphere and Drug Therapy (Elsevier, 1984); Kwon et al, *J. Colloid Interface Sci.* 143:501, 1991; Cremers et al, *J. Controlled Rel.* 11:167, 1990; Codde et al., *Anti-cancer Res.* 10:1715–1718, 1990 and WO 94/27576.

Preferably, a formulation having a release profile as provided herein contains multiple different units in a single, multiple-unit dosage form. Each unit typically displays a different release profile. For example, a formulation may contain two or three units. The first unit may be an immediate release ("IR") unit, which releases active component rapidly upon administration in order to generate the plasma concentration at $Tmax_1$. An optional component may be a sustained release unit which provides extended release of the active component to ensure that the plasma concentration of the sedative-hypnotic compound does not fall below the minimum effective concentration to maintain sleep at Tmin. The second unit may be a delayed release unit in which active component is released, at in least in part, in a burst akin to the first IR unit, but at a specified period of time following administration in order to generate the plasma concentration at $Tmax_2$. The use of additional delayed/controlled release units may also be employed, provided the plasma profile of this invention results. The individual units may comprise powder, granule and/or pellet formulations, and are preferably formulated as pellets. The multiple-unit dosage form can be, for example, a compressed tablet or hard gelatin capsule.

A first unit formulated for immediate release dosage may comprise a surface-active agent such as sodium lauryl sulfate, sodium monoglycerate, sorbitan monooleate, polyoxyethylene sorbitan monooleate, glyceryl monostearate, glyceryl monooleate, glyceryl monobutyrate, any one of the Pluronic line of surface-active polymers, or any other suitable material with surface active properties or any combination of the above. Preferably the surface-active agent is sodium lauryl sulfate. The concentration of surface-active agent in this unit can range from about 0.05 to about 10.0% (W/W). A first unit in pellet form may be made via any suitable process that generates a reasonably round unit. This process can be, for example, simple granulation, followed by sieving; extrusion and marumerization; rotogranulation; or any agglomeration process which results in a pellet of reasonable size and robustness. This immediate release unit may alternatively be formulated as a granule or powder, although the preferred form is a pellet due to mixing and de-mixing considerations.

Materials to be admixed along with the drug and surfactant for a first pellet should possess sufficient binding properties to allow agglomeration to occur. Such materials can be, but are not limited to, microcrystalline cellulose (such as Avicel), corn starch, pregelatinized starch (such as Starch 1500 or National 1551), potato starch, sodium carboxymethylated starch, sodium carboxymethylated cellulose, hydroxypropylmethyl cellulose, hydroxypropylcellulose, hydroxyethylcellulose, ethylcellulose, as well as any cellulose ether. In addition, any binder material such as gums (e.g., guar gum) natural binders and derivatives such as alginates, chitosan, gelatin and gelatin derivatives, are also useful. Synthetic polymers such as polyvinylpyrrolidone (PVP), acrylic acid derivatives (Eudragit, Carbopol, etc.) and polyethylene glycol (PEG) are also useful as binders and matrix formers for the purpose of this invention. It may be useful to have these materials present in the range of from about 1.0 to about 60.0% (W/W) either in total, or individually in combination with one another. Preferably, such materials should be present in the range of from about 30 to about 50 percent (W/W). It may also be desirable to incorporate a disintegrant into these pellets in order to facilitate dissolution of the active ingredient. For this purpose, any suitable tablet disintegrant can be utilized here, such as cross-linked sodium carboxymethylcellulose (Ac-Di-Sol), cross-linked sodium carboxymethyl starch (Explotab, Primojel), cross-linked PVP (Plasdone XL) or any other material possessing tablet disintegrant properties.

The optional unit, when present, generally has a sustained or prolonged release profile. This unit should have all of the ingredients as mentioned above, but in different ratios, depending on the desired release profile. The process for manufacturing such units may be as described above described above for the intermediate-release pellet. In addition, this unit may have a controlling coat applied to the surface of the pellet such that the release of the drug from the pellet can be further controlled and released over a period such that the plasma concentration of the drug does not fall below the minimum effective concentration to maintain sleep at Tmin. The materials used for this purpose can be, but are not limited to, ethylcellulose, hydroxypropylmethylcellulose, hydroxypropylcellulose, hydroxyethylcellulose, methylcellulose, nitrocellulose, carboxymethylcellulose, and any other cellulose ether, as well as copolymers of ethacrylic acid and methacrylic acid (Eudragit), or any other acrylic acid derivative (Carbopol, etc.) can be used. In addition, an enteric coating material can also be employed, either singularly, or in combination with one or more of the above non-pH sensitive coatings. Enteric coating materials include, but are not limited to, hydroxypropylmethylcellulose phthalate and the phthalate esters of all the cellulose ethers, as well as phthalate esters of the acrylic acid derivatives (Eudragit) and cellulose acetate phthalate. These coating materials can be employed in coating the surfaces in a range of from about 1.0% (W/W) to about 25% (W/W). Preferably these coating materials should be in a range of from about 2.0 to about 12.0 percent (W/W).

A second unit in the controlled-release formulation may be qualitatively similar to the first unit, and may be produced by a manufacturing process as described above. However, such a unit may have an internal component (e.g., an enteric or pH sensitive material) that breaks down in the pH of the lower GI tract. This material can comprise a substance such as, but not limited to, cellulose acetate phthalate, hydroxypropylmethylcellulose phthalate, any additional cellulose ether phthalates, any of the acrylic acid derivative phthalates (Eudragit), as well as any enteric coating material, such as shellac, zein or others. The concentration of such materials in the unit should be from about 1.0 to about 15.0% (W/W), preferably the concentration of materials should be from about 2.0 to about 10.0 percent (W/W). Suitable coating materials may be similar to the coating for the optional unit, except that it may have a considerable pH sensitivity associated with it. More specifically, it is desirable to coat this unit with any of the pH sensitive or enteric coating materials listed above, either singularly, or in combination with any coating material mentioned above. The coating level of this unit should range from about 1.0 to about 15.0% (W/W), preferably the concentration of materials should be from about 2.0 to about 12.0 percent (W/W).

Each of the above units, all of which are preferably pellets, should have its own dissolution profile associated with the formulation assigned to it. Depending on the formulation chosen in this invention, the exact ratios of each of the pellets may need to be adjusted. In general, the amount of first unit in the formulation ranges from about 30% to about 70%. The amount of optional unit in the dosage form preferably ranges from about 0 to about 20%. The amount of second unit preferably ranges of from about 30% to about 70%. The release profile of the formulations may be adjusted by, for example, varying the thickness of the coating, changing the particular release retardant used, altering the relative amounts of coating components, including additional ingredients or by modifying the method of manufacture. The variation of such parameters to adjust the release profile is well known in the art.

To assess the plasma concentration time profiles, plasma concentration, Tmax and Tmin may be determined using well known techniques. Briefly, blood samples are taken from a patient over the course of the dosing interval. The samples are then tested to determine the plasma level of the hypnotic compound. Any suitable assay may be used to determine plasma levels, such as ELISA, RIA, or chromatography (e.g., gas-liquid chromatography or high pressure liquid chromatography) linked to any suitable detection system such as UV, fluorescence, mass spectrometry or an electrochemical system).

As noted above, a formulation may comprise active sedative-hypnotic compound or may comprise a precursor thereof. In either case, the plasma levels assessed are those of active sedative-hypnotic compound. For formulations that comprise an active compound, assays are designed to detect the sedative-hypnotic contained within the formulation. For formulations that comprise a precursor that is metabolized to generate active compound, an active metabolite is assayed. Active metabolites may be identified using well known techniques.

To assess sedative activity, any of a variety of standard assays may be used. For example, sedative activity may be assessed using tests such as EEG measurements, subjective reporting, visual analogue scales, critical flicker fusion, Salford tracking, sway tests, sleep efficiency, time to sleep onset, time to awakenings number of awakenings and/or sleep architecture.

For NBI-34060, a preferred method for assaying plasma levels is an HPLC procedure. This method also permits detection of the primary inactive metabolite N-[3-[3-(2-thienylcarbonyl)-pyrazolo-[1,5-a]-pyrimidin-7-yl)-phenylacetamide and is sufficiently sensitive to detect NBI-34060 in samples obtained from patients treated with low doses for up to 4–6 half-lives. Briefly, a plasma sample (e.g., 100 ?1) diluted (e.g., 1:4) and combined with internal standard. The mixture is vortexed and centrifuged to obtain a clear supernatant. Samples are then evaporated to dryness and reconstituted with a buffer suitable for HPLC (e.g., phosphate buffer pH 6.8). The samples (e.g., 50 l) may then be injected under appropriate conditions. For example, using a Hewlett Packard Zorbax, C8, 4.6×150 mm column, the following chromatographic conditions may be used:

| Method Type: | Isocratic |
|---|---|
| Mobile Phase: | 40% ACN; 60% Phosphate Buffer |
| Mobile Phase Flow Rate: | 1.0 ml/min |
| Detection: | Fluorescence detection |
| Excitation wavelength: | 345 nm |
| Emission wavelength: | 460 nm |

Under these conditions, approximate retention times are 4.8 minutes for the metabolite and 5.8 minutes for NBI-34060.

FIG. 1 illustrates a representative release profile of the formulations described herein. Referring to FIG. 1, $Tmax_1$ occurs at approximately 1 hour post-administration, Tmin occurs at approximately 2 hours post-administration, and $Tmax_2$ occurs at approximately 3 hours post-administration. Further representative release profiles are set forth below in the Examples.

A hypnotic formulation is generally formulated and administered to exert a therapeutically useful effect while minimizing undesirable side effects. The number and degree of acceptable side effects depend upon the condition for which the composition is administered. The concentration of active component in the composition will depend on absorption, inactivation and excretion rates thereof, the dosage schedule and the amount administered, as well as other factors that may be readily determined by those of skill in the art.

The sedative-hypnotic formulations provided herein may be used for therapy of conditions such as insomnia, anxiety and convulsions. Patients afflicted with such conditions may be readily diagnosed using standard clinical criteria. It will be apparent to those of ordinary skill in the art that formulations comprising other active components, with similar release profiles, may further be used to treat any condition in which such a release profile is desirable. Typically, such conditions are those in which sustained nocturnal release of a drug is desired. Formulations as provided herein may be administered to a patient, alone or in combination with other therapies, to treat or prevent such conditions.

Appropriate dosages and a suitable duration and frequency of administration will be determined by such factors as the nature of the hypnotic compound used, the type and severity of the patient's condition and the method of administration. In general, an appropriate dosage and treatment regimen provides the formulation in an amount sufficient to provide therapeutic and/or prophylactic benefit (i.e., an amount that ameliorates the symptoms or treats, delays or prevents progression of the condition). The precise dosage and duration of treatment may be determined empirically using known testing protocols or by testing the compositions in model systems known in the art and extrapolating therefrom. Known testing protocols include, but are not limited to, EEG measurements, subjective reporting, visual analogue scales, critical flicker fusion, Salford tracking, sway tests, sleep efficiency, time to sleep onset, time to awakenings number of awakenings and sleep architecture. Dosages may also vary with the severity of the condition to be alleviated. In general, the use of the minimum dosage that is sufficient to provide effective therapy is preferred. Patients may generally be monitored for therapeutic effectiveness using assays (which my be analytical or behavioral/psychometric) that are suitable for the condition being treated or prevented. Such assays will be apparent to those of ordinary skill in the art, and for any particular subject, specific dosage regimens may be adjusted over time according to the individual need. For NBI-34060, a suitable clinical dose is generally 1–100 mg, preferably 5–60 mg and more preferably 25–50 mg, with the total dose dependent on the formulation used and the clinical result to be achieved.

The following Examples are offered by way of illustration and not by way of limitation.

EXAMPLES

Examples 1–29

Preparation of Controlled-Release Formulation

This Example illustrates the preparation of representative controlled-release formulations comprising NBI-34060.

A. First Unit (Pellet A: Immediate Release Component)

| Example | Component | Weight Percent | Kilograms |
|---|---|---|---|
| 1 | Microcrystalline Cellulose, N.F. (MCC) (Avicel PH-101/102, Emcocel, etc.) | 75.0 | 0.75 |
|  | Hydroxypropylmethylcellulose (HPMC)(Methocel E5/E50/K5/K50) | 5.0 | 0.05 |
|  | Croscarmellose, Type A, N.F. (Ac-Di-Sol) | 5.0 | 0.05 |
|  | Sodium Lauryl Sulfate (SLS) | 5.0 | 0.05 |
|  | NBI-34060 | 10.0 | 0.1 |
|  | TOTAL | 100.0 | 1.000 |
| 2 | MCC | 64.0 | 0.64 |
|  | Polyvinylpyrollidone (PVP; Plasdone) | 5.0 | 0.05 |
|  | Sodium Starch Glycolate, N.F. (Explotab, Primojel) | 8.0 | 0.08 |
|  | SLS | 8.0 | 0.08 |
|  | NBI-34060 | 15.0 | 0.15 |
|  | TOTAL | 100.0 | 1.000 |
| 3 | MCC | 20.0 | 0.2 |
|  | Pre-gelatinized Starch (STARCH 1500, National 1551) | 15.0 | 0.15 |
|  | Croscarmellose | 5.0 | 0.05 |
|  | Corn Starch, U.S.P. (as paste) | 5.0 | 0.05 |
|  | Dioctyl Sodium Sulfosuccinate (DSS) | 5.0 | 0.05 |
|  | NBI-34060 | 50.0 | 0.50 |
|  | TOTAL | 100.0 | 1.000 |
| 4 | MCC | 20.0 | 0.20 |
|  | MCC/Carboxymethyl Cellulose (CMC) (Avicel RC Grade) | 20.0 | 0.20 |
|  | Croscarmellose | 5.0 | 0.05 |
|  | SLS | 5.0 | 0.05 |
|  | NBI-34060 | 50.0 | 0.50 |
|  | TOTAL | 100.0 | 1.000 |
| 5 | MCC/CMC | 20.0 | 0.2 |
|  | Croscarmellose | 5.0 | 0.05 |
|  | Sodium Starch Glycolate | 5.0 | 0.05 |
|  | HPMC | 5.0 | 0.05 |
|  | DDS | 1.0 | 0.01 |
|  | NBI-34060 | 64.0 | 0.64 |
|  | TOTAL | 100.0 | 1.000 |
| 6 | MCC | 35.0 | 0.35 |
|  | MCC/CMC | 25.0 | 0.25 |
|  | Croscarmellose | 10.0 | 0.10 |

-continued

A. First Unit (Pellet A: Immediate Release Component)

| Example | Component | Weight Percent | Kilograms |
|---|---|---|---|
| | DDS | 1.0 | 0.10 |
| | NBI-34060 | 29.0 | 0.29 |
| | TOTAL | 100.0 | 1.000 |
| 7 | MCC/CMC | 60.0 | 0.60 |
| | Polyacrylic Acid (Carbomer) | 8.0 | 0.08 |
| | SLS | 5.0 | 0.05 |
| | Sodium Starch Glycolate | 10.0 | 0.10 |
| | NBI-34060 | 17.0 | 0.17 |
| | TOTAL | 100.0 | 1.000 |
| 8 | MCC | 60.0 | 0.60 |
| | HPMC | 5.0 | 0.05 |
| | Croscarmellose | 5.0 | 0.05 |
| | Sodium bis-(2-ethylhexyl)sulfo-succinate (Aerosol OT) | 2.0 | 0.02 |
| | NBI-34060 | 28.0 | 0.28 |
| | TOTAL | 100.0 | 1.000 |
| 9 | MCC | 35.0 | 0.35 |
| | HPMC | 5.0 | 0.05 |
| | Mono/Di/Tri-glyceride Mixture (Atmul-84S) | 20.0 | 0.2 |
| | SLS | 2.0 | 0.02 |
| | NBI-34060 | 38.0 | 0.38 |
| | TOTAL | 100.0 | 1.000 |
| 10 | MCC | 25.0 | 0.25 |
| | Polyvinylpyrrolidone (PVP) (Plasdone) | 5.0 | 0.05 |
| | Glyceryl Monostearate (Myvaplex) | 15.0 | 0.15 |
| | SLS | 2.5 | 0.025 |
| | NBI-34060 | 52.5 | 0.525 |
| | TOTAL | 100.0 | 1.000 |

B. Optional Unit (Pellet B: Sustained Release Component)

| Example | Component | Weight Percent | Kilograms |
|---|---|---|---|
| 11 | Core: MCC | 30.0 | 0.3 |
| | HPMC | 10.0 | 0.10 |
| | Glyceryl Monostearate | 10.0 | 0.10 |
| | SLS | 1.5 | 0.015 |
| | NBI-34060 | 48.5 | 0.485 |
| | TOTAL | 100.0 | 1.000 |
| | Coating: Methacrylic Acid Copolymer (Eudragit RS) | 45.0 | 0.45 |
| | Methacrylic Acid Copolymer (Eudragit RL) | 45.0 | 0.45 |
| | Triethyl Citrate | 9.0 | 0.09 |
| | Fumed Silica | 1.0 | 0.01 |
| | TOTAL | 100.0 | 1.000 |
| 12 | Core pellet as in Example 11 | | |
| | Coating: HPMC (Methocel E50) | 45.0 | 0.45 |
| | Ethylcellulose (Ethocel) | 45.0 | 0.45 |
| | Polyethylene Glycol 400 (PEG400) | 10.0 | 0.10 |
| | TOTAL | 100.0 | 1.000 |
| 13 | Core pellet as in Example 11 | | |
| | Coating: HPMC | 20.0 | 0.20 |
| | Ethylcellulose | 70.0 | 0.70 |
| | PEG400 | 10.0 | 0.10 |
| | TOTAL | 100.0 | 1.000 |

-continued

B. Optional Unit (Pellet B: Sustained Release Component)

| Example | Component | Weight Percent | Kilograms |
|---|---|---|---|
| 14 | Core: MCC | 15.0 | 0.15 |
| | MCC/CMC Mixture | 15.0 | 0.15 |
| | HPMC | 20.0 | 0.20 |
| | DSS | 1.0 | 0.01 |
| | NBI-34060 | 49.0 | 0.49 |
| | TOTAL | 100.0 | 1.000 |
| | Coating: HPMC (Methocel K5M) | 10.0 | 0.10 |
| | HPMC (Methocel E50) | 14.0 | 0.14 |
| | Ethylcellulose | 66.0 | 0.66 |
| | PEG400 | 10.0 | 0.10 |
| | TOTAL | 100.0 | 1.000 |
| 15 | Core pellet as in Example 14 | | |
| | Coating as in Example 11 | | |
| 16 | Core pellet as in Example 14 | | |
| | Coating as in Example 12 | | |
| 17 | Core pellet as in Example 14 | | |
| | Coating as in Example 13 | | |
| 18 | Core: MCC | 30.0 | 0.3 |
| | PVP | 10.0 | 0.10 |
| | Mono/Di/Tri-Glyceride Mixture | 10.0 | 0.10 |
| | SLS | 5.0 | 0.05 |
| | NBI-34060 | 45.0 | 0.45 |
| | TOTAL | 100.0 | 1.000 |
| | Coating as in Example 11 | | |
| 19 | Core pellet as in Example 18 | | |
| | Coating as in Example 12 | | |
| 20 | Core pellet as in Example 18 | | |
| | Coating as in Example 13 | | |
| 21 | Core pellet as in Example 18 | | |
| | Coating as in Example 14 | | |

C. Second Unit (Pellet C: Delayed Release IR Component)

| Example | Component | Weight | Kilograms |
|---|---|---|---|
| 22 | Core: MCC | 30.0 | 0.30 |
| | Hydroxypropylmethylcellulose Phthalate (HPMCP) | 10.0 | 0.10 |
| | Glyceryl Monostearate | 7.5 | 0.075 |
| | SLS | 5.0 | 0.05 |
| | NBI-34060 | 47.5 | 0.475 |
| | TOTAL | 100.0 | 1.000 |
| | Coating: Cellulose Acetate Phthalate (CAP) | 60.0 | 0.60 |
| | Ethylcellulose | 25.0 | 0.25 |
| | PEG400 | 15.0 | 0.15 |
| | TOTAL | 100.0 | 1.000 |
| 23 | Core pellet as in Example 22 | | |
| | Coating: Methacrylic Acid Copolymer (Eudragit L100-55) | 85.0 | 0.85 |
| | Triethyl Citrate | 14.0 | 0.14 |
| | Talc | 1.0 | 0.01 |
| | TOTAL | 100.0 | 1.000 |
| 24 | Core pellet as in Example 22 | | |
| | Coating: CAP | 65.0 | 0.65 |
| | HPMCP | 15.0 | 0.15 |
| | PEG 400 | 10.0 | 0.10 |
| | PEG 8000 | 10.0 | 0.10 |
| | TOTAL | 100.0 | 1.000 |
| 25 | Core: MCC | 35.0 | 0.35 |
| | Mono/Di/Tri-Glyceride Mixture | 15.0 | 0.15 |
| | CAP | 10.0 | 0.10 |

C. Second Unit (Pellet C: Delayed Release IR Component)

|    |                          | Weight | Kilograms |
|----|--------------------------|--------|-----------|
|    | DSS                      | 1.0    | 0.01      |
|    | NBI-34060                | 39.0   | 0.39      |
|    | TOTAL                    | 100.0  | 1.000     |
|    | Coating as in Example 22 |        |           |
| 26 | Core pellet as in Example 25 |    |           |
|    | Coating as in Example 23 |        |           |
| 27 | Core pellet as in Example 25 |    |           |
|    | Coating as in Example 24 |        |           |
| 28 | Core pellet as in Example 25 |    |           |
|    | Coating: Shellac         | 85.0   | 0.85      |
|    | Mineral Oil              | 13.0   | 0.13      |
|    | SLS                      | 0.5    | 0.005     |
|    | Talc                     | 1.5    | 0.015     |
|    | TOTAL                    | 100.0  | 1.000     |
| 29 | Core pellet as in Example 22 |    |           |
|    | Coating as in Example 28 |        |           |

Each unit may be formulated as a pellet by combining the drug substance and other pellet forming excipients. All components are dispensed, weighed, screened and added to an appropriate-sized blender. The ingredients are mixed and water or other suitable solvents are added until a uniform, wet mass is formed. The wet mass is extruded through a perforated screen using appropriate extrusion equipment. The extrudate is further processed on a spheronizer, which transforms the extrudate into uniform, spherical pellets. The pellets are tray dried in a suitable oven or, alternatively, using other suitable fluidized bed drying equipment.

For coated units, the coating excipients are dispensed, weighed, and added to an appropriate-sized container. The mixture is stirred until a uniform dispersion is formed. Using appropriate fluidized bed coating equipment, the pellets are placed in the fluidized bed apparatus. The pellets are coated with the coating suspension and simultaneously dried.

To assemble a final dosage form, the various units (one or more pellets from 1–3 of the above categories) are filled in the correct ratios into hard gelatin capsules using appropriate capsule filling equipment. In one such dosage form, the pellet of Example 1 is combined with the pellet of Example 13 in a 1:1 ratio. Pellets from Examples 1 and 13 are mixed in an appropriate dry blender. Additional ingredients are added, such as MCC and magnesium stearate, to facilitate tablet compression and lubrication. The mixture is blended and the mix is compressed on a suitable tablet press. cl Examples 30

Representative IR/Delay Release IR Formulation

This Example illustrates a preferred sedative-hypnotic formulation of the present invention, in tablet form, utilizing a dual IR formulation—that is, 20 mg IR and 20 mg IR with a 2 hour delay.

| Example | Component | Mg per Tablet | Weight % |
|---------|-----------|---------------|----------|
| 30 | Core Tablet (Delayed IR) | | |
|   | NBI-34060 (micronized) | 20.0 | 8.0 |
|   | Colloidal Silicon Dioxide, USP (Cab-O-Sil M5-P) | 1.25 | 0.5 |
|   | Lactose Monohydrate, NF (Fast-Flo 316) | 220.0 | 88.0 |
|   | Croscarmellose Sodium, NF (Ac-di-Sol) | 7.5 | 3.0 |
|   | Magnesium Stearate, NF | 1.25 | 0.5 |
|   | Total (Core Tablet) | 250.0 | 100.0 |
|   | Tablet Coat (Delayed Release)** | | |
|   | Surelease (24.5% Solids Suspension) | 15.0 | |
|   | Purified Water, USP* | * | |
|   | Tablet Coat (IR) | | |
|   | NBI-34060 (micronized) | 20.0 | 42.1 |
|   | Sodium Lauryl Sulfate, USP (Supralate C) | 5.0 | 10.5 |
|   | Mannitol 60 | 22.5 | 47.4 |
|   | Purified Water, USP* | * | * |
|   | Total (Tablet Coat-Active) | 47.5 | 100.0 |
|   | Tablet Coat (Cosmetic) | | |
|   | Opadry White | 8.9 | 3.0 |
|   | Purified Water | * | * |
|   | Total (Tablet Coat-Cosmetic | 8.9 | 100 |

*Purified Water, USP is evaporated during the drying process
**Coating solution prepared in excess to account for manufacturing losses Examples 31

Representative Plasma Profiles IR/Delay Release IR Formulation

Figure 2A:
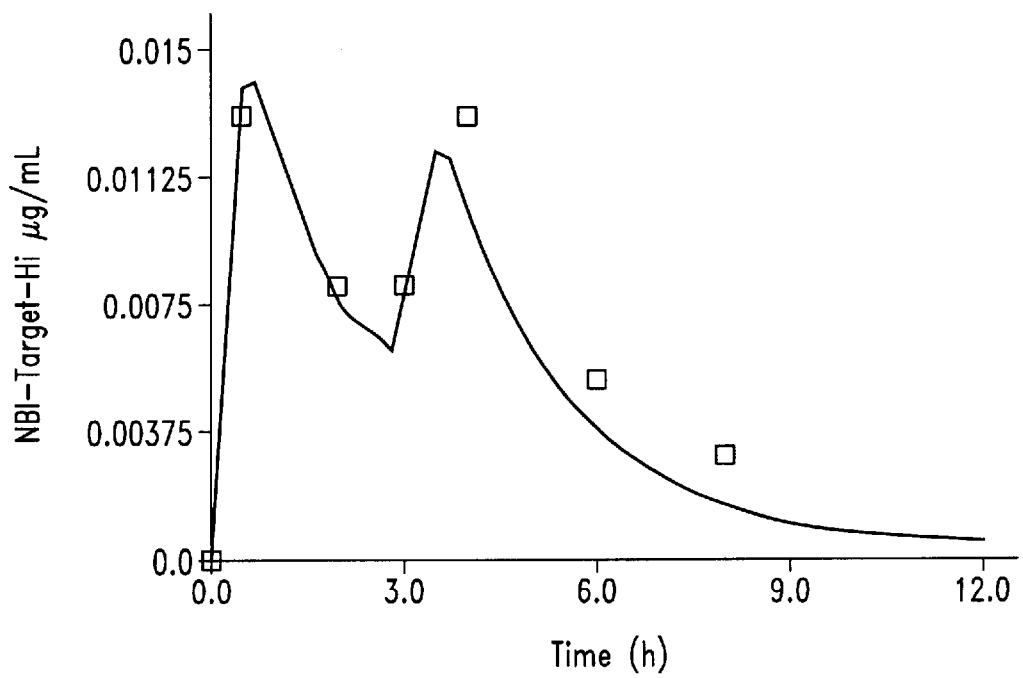
Figure 2B:
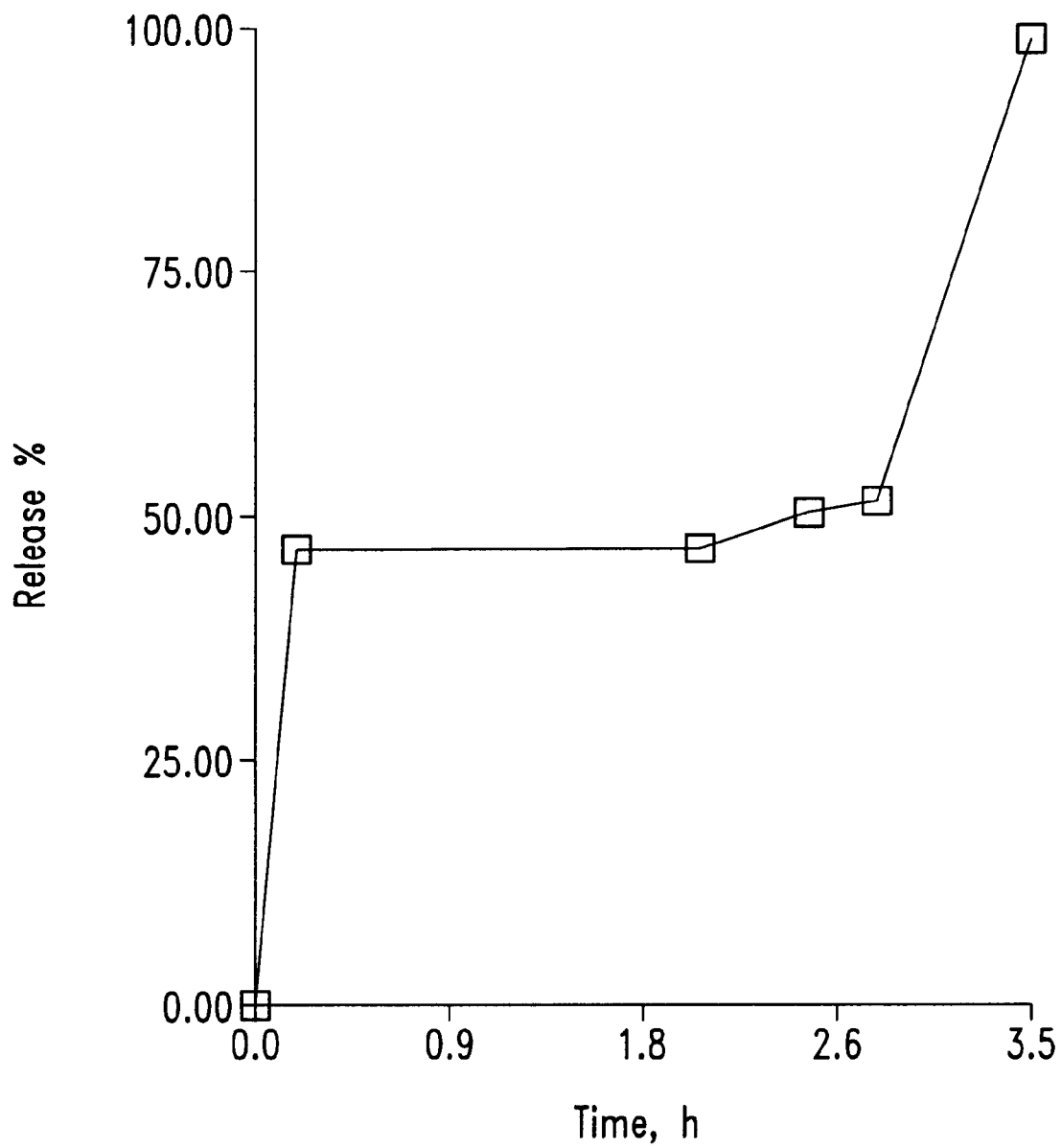
FIGS. 2B and 3B illustrate the corresponding calculated dissolution curves of the same.
Figure 3A:
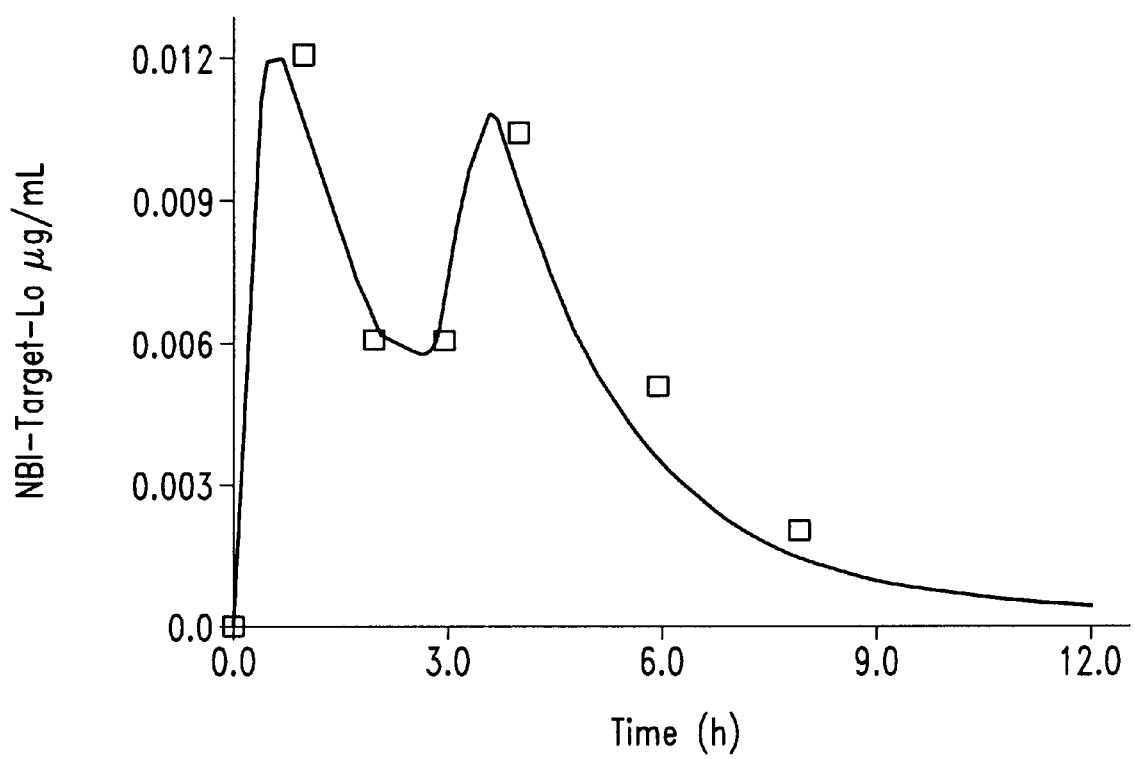
Figure 3B:
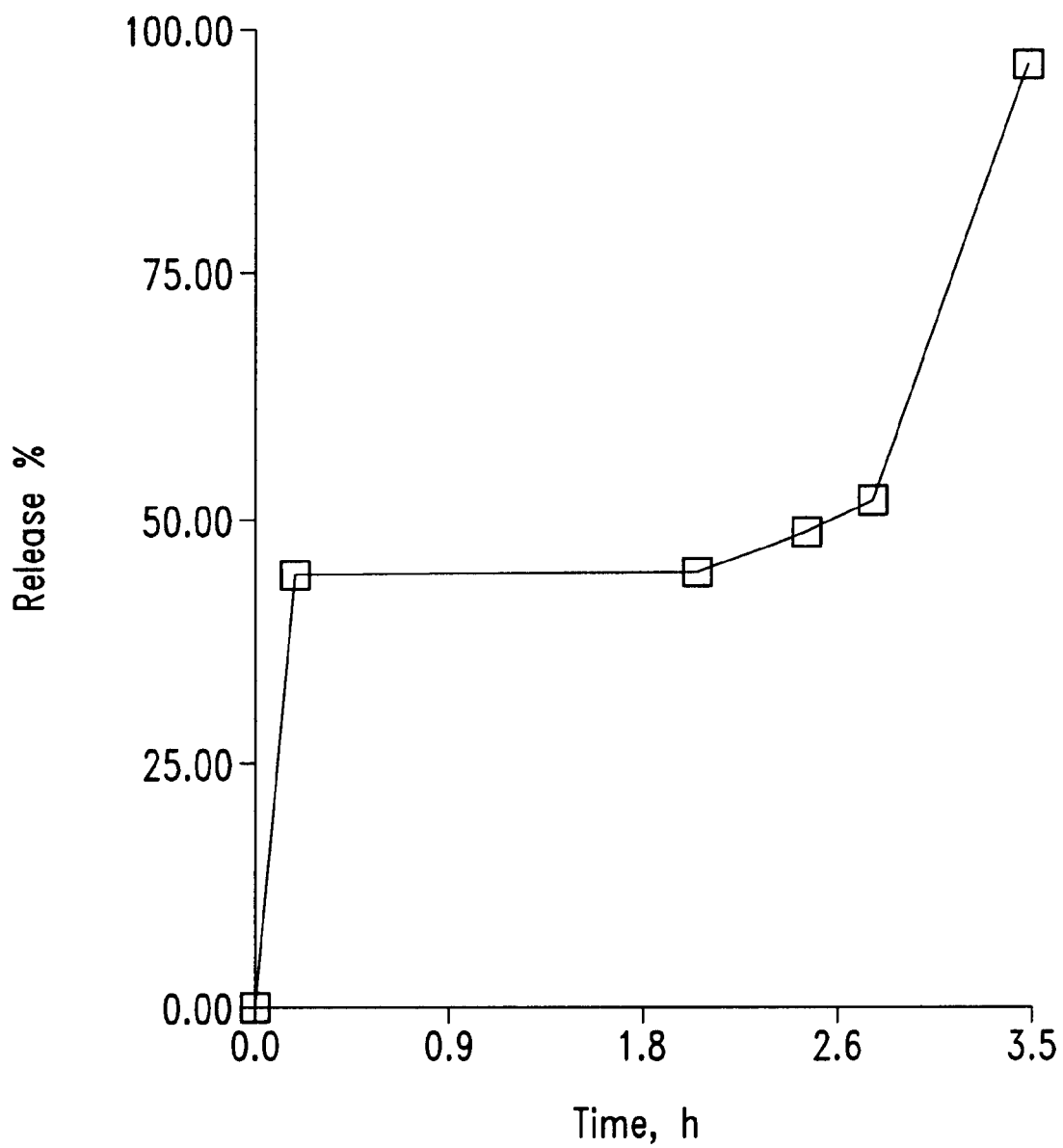
Figure 4A:
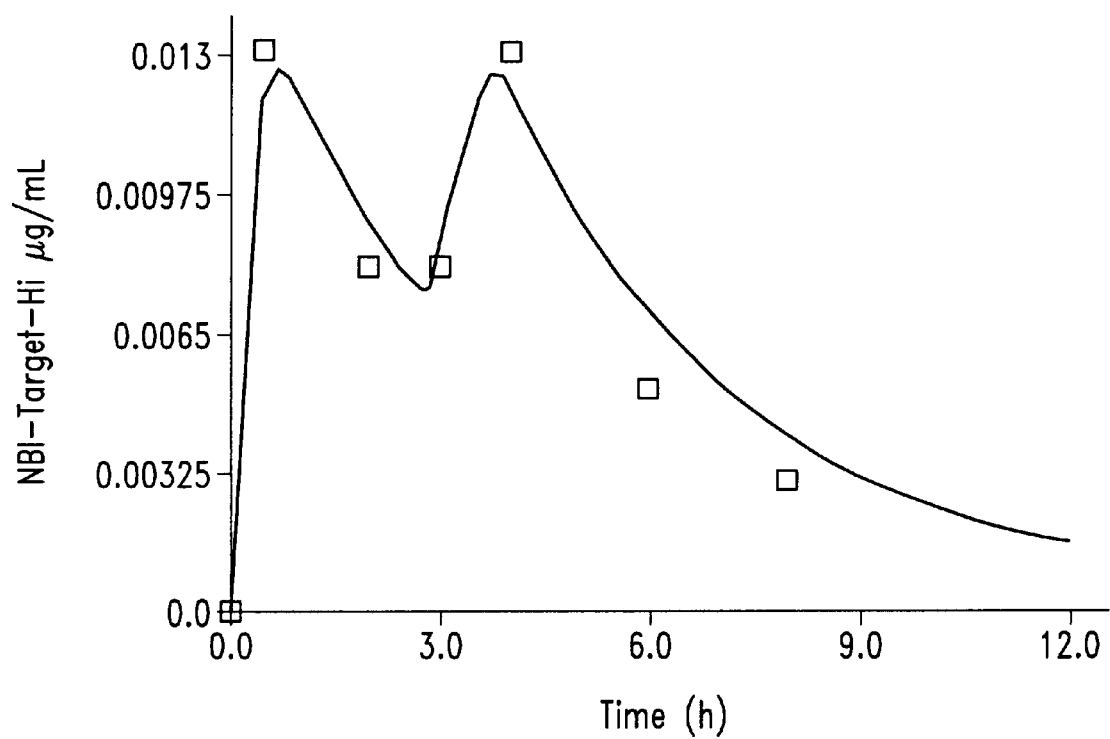
Figure 4B:
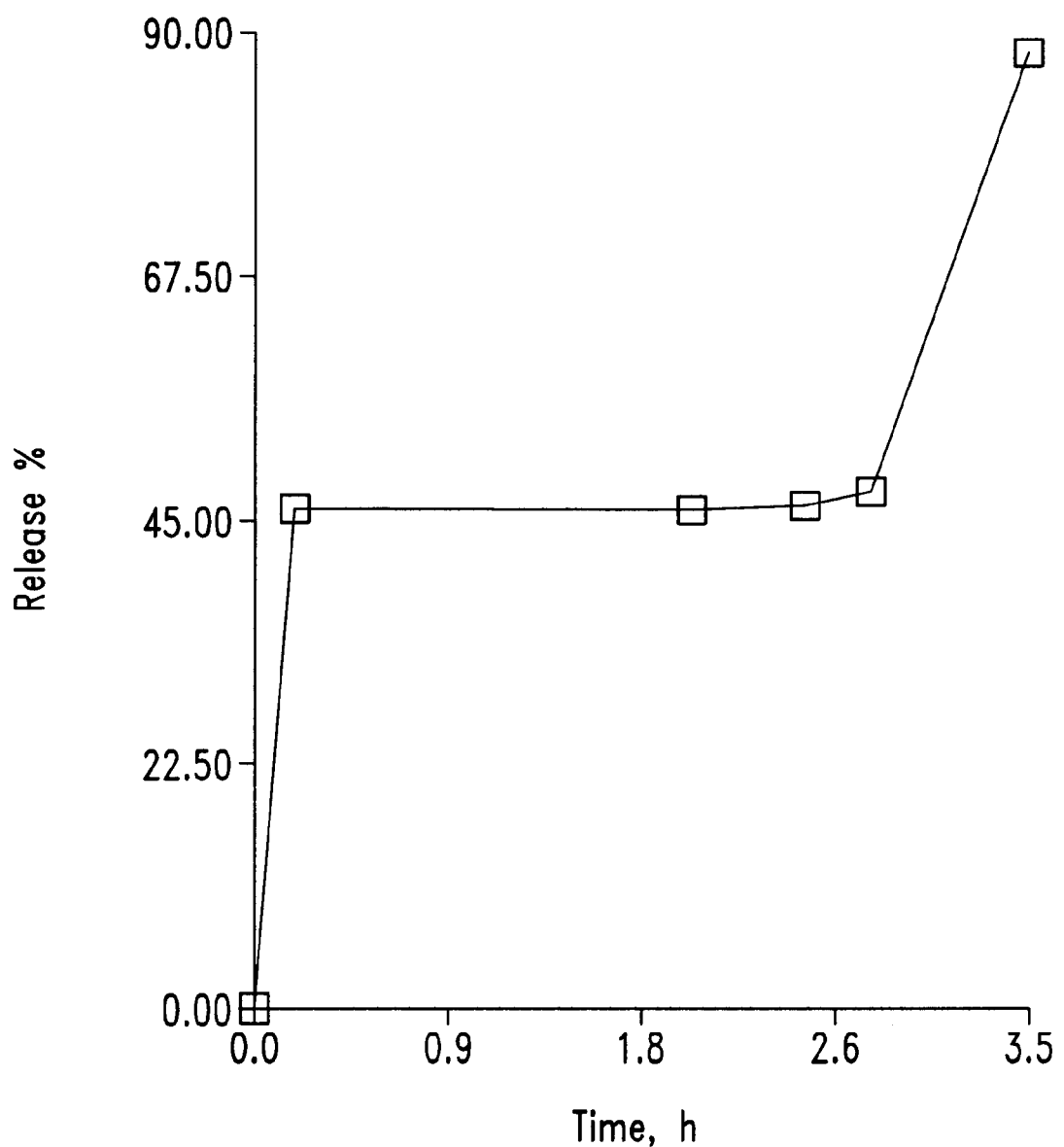
FIGS. 4B and 5B illustrate the corresponding calculated dissolution curves of the same.
Figure 5A:
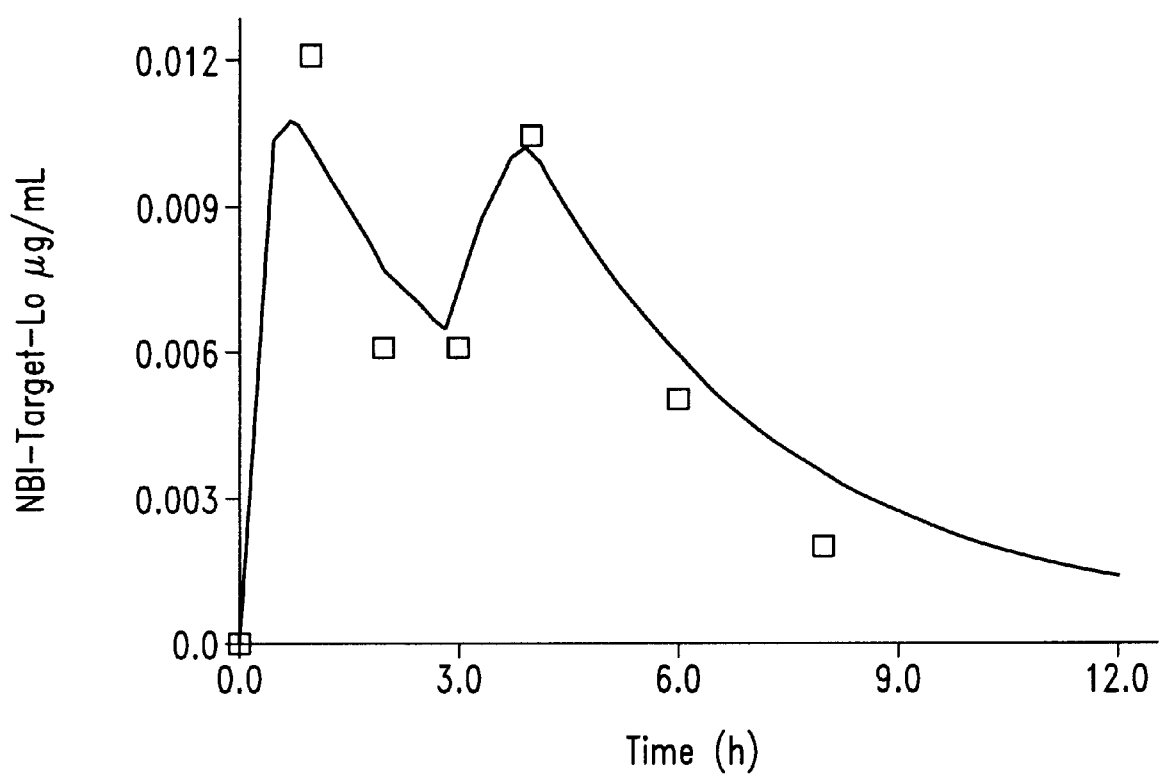
Figure 5B:
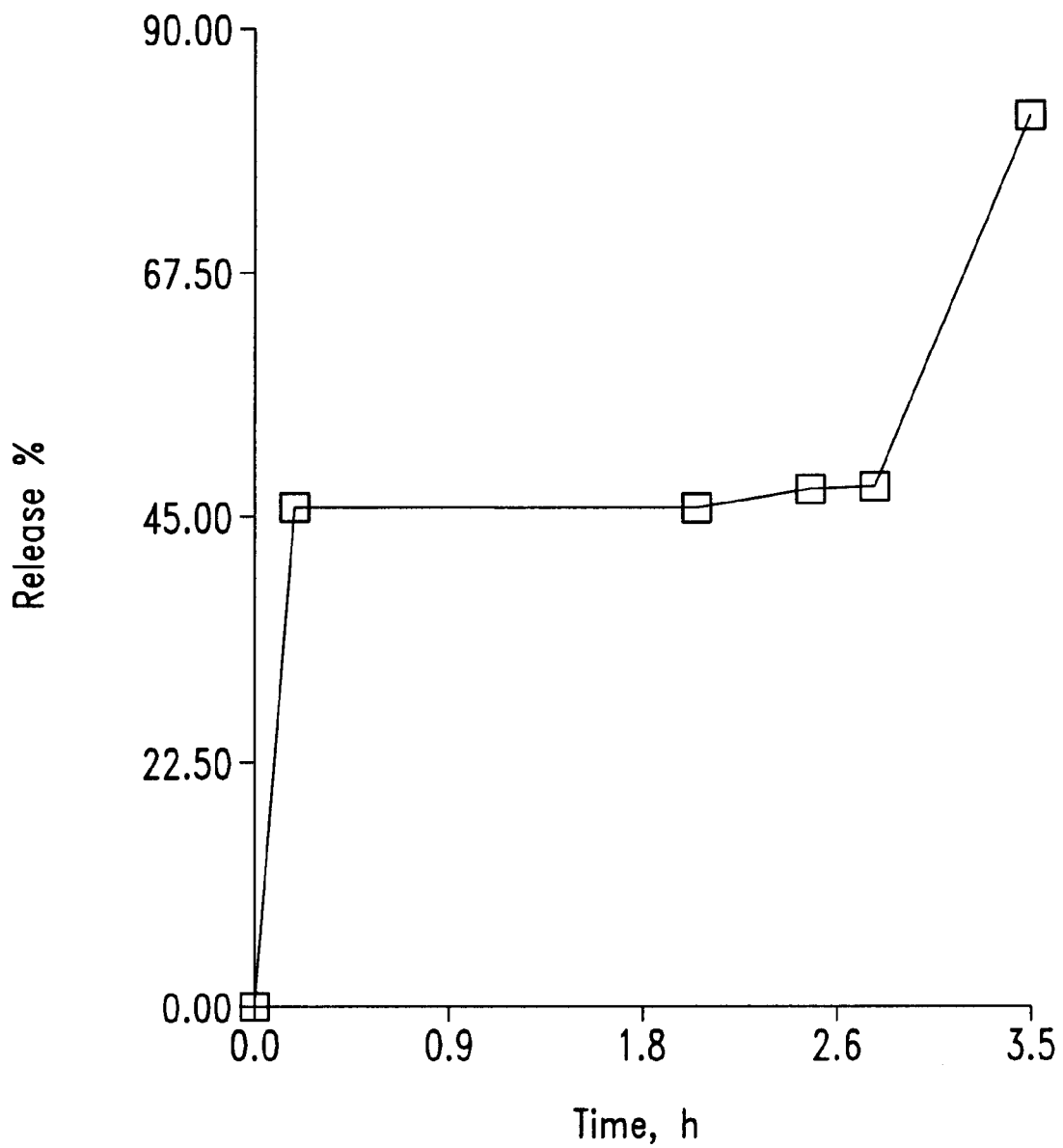

This Example illustrates simulated plasma profiles of representative sedative-hypnotic compound of the present invention having a half-life of 1.3 hours, compared to a sedative-hypnotic compound having a half-life of 2.3 hours. In this experiment, commercially available plasma profiling software (GastroPlus™) (Simulations Plus Inc., CA.) was used to simulate the effects of varying controlled release profiles and pharmacokinetic parameters based on in vivo plasma concentrations of NBI-34060 as measured in 12-healthy male human subjects. Adjustment in half-life from 1.3 to 2.3 hours was made by changing clearance (CL) in a one-compartment pharmacokinetic model, with volume of distribution (Vd) held at 159.25 L (or 2.275 L/kg, assuming 70 kg subject weight). This assumed that the lower CL drug would distribute to the same tissues as the higher CL drug, so that all half-life changes were because of differences in metabolism and/or renal clearance rather than in volumes. Two oral plasma concentration-time files were created (NBI-Target-Hi.opd and NBI-Target-Lo.opd) with plasma concentration-time points serving as targets (shown as a square in FIGS. 2, 3, 4 and 5). The requirements for $Tmax_2$ for the high target was set at 100% of $Tmax_1$.

for the NBI-Target-Hi.opd file:

(a) 13 ng/mL at $T_{max1}$=0.5 hour (b) 8 ng/mL at times of 2 and 3 h (c) 13 ng/mL at $T_{max\ 2}$=4.0 h (d) 5.2 ng/mL at 6 h (e) 3 ng/mL at 8 h (B) for the NBI-Target-Lo.opd file:

(a) 12 ng/mL at $T_{max1}$=1 hour (b) 6 ng/mL at times of 2 and 3 h (c) 10.4 ng/mL at $Tmax_2$ =4 h (f) 5 ng/mL at 6 h (g) 2 ng/mL at 8 h FIGS. 2A and 3A illustrate the plasma concentrations achieved with a sedative-hypnotic compound of the present invention, having a half-life of 1.3 hours, with FIG. 2A depicting the "Target High" profile (50 mg dosage) and FIG. 3A depicting the target low profile (45 mg dosage). FIGS. 2B and 3B illustrate the corresponding calculated dissolution curves for the formulations of FIGS. 2A and 3A, respectively. Similarly, FIGS. 4A and 5A illustrate the plasma concentrations achieved with a sedative-hypnotic compound outside the scope of this invention, having a half-life of 2.3 hours. FIG. 4A depicts the "Target High" profile (41 mg dosage) and FIG. 5A depicts the target low profile (35 mg dosage). FIGS. 4B and 5B illustrate the corresponding calculated dissolution curves for the formulations of FIGS. 4A and 5A, respectively. To this end, it should be noted that the pulsed plasma concentration profile of this invention could not be achieved with a sedative-hypnotic compound having a half-life of 2.3 hours. Most noticeably, the plasma concentrations, while sufficiently high at 6 hours post-administration, does not fall to sufficiently low level by 8 hours post-administrations, even though considerably less compound was utilized in the t1/2=2.3 hour formulations.

Example 32

Preparation of NBI-34060 By Large-Scale Synthesis

As noted above, NBI-34060 may be made according to known techniques, such as those disclosed in U.S. Pat. No. 4,521,422. In that patent an appropriately substituted pyrazole (a) is reacted with an appropriately substituted 3-dimethylamino-2-propen-1-one (b) as represented by the following reaction scheme:

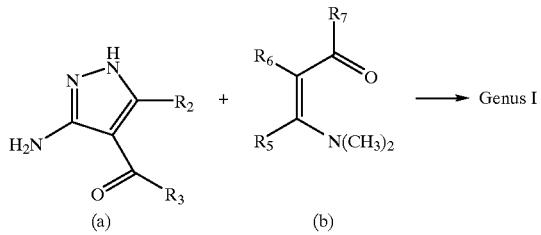

Genus I is as described above, yields NBI-34060 when $R_2$, $R_5$ and $R_6$ are hydrogen, $R_3$ is thienyl, and $R_7$ is 2-(N(Me)COCH$_3$)-phenyl.

Figure 6:
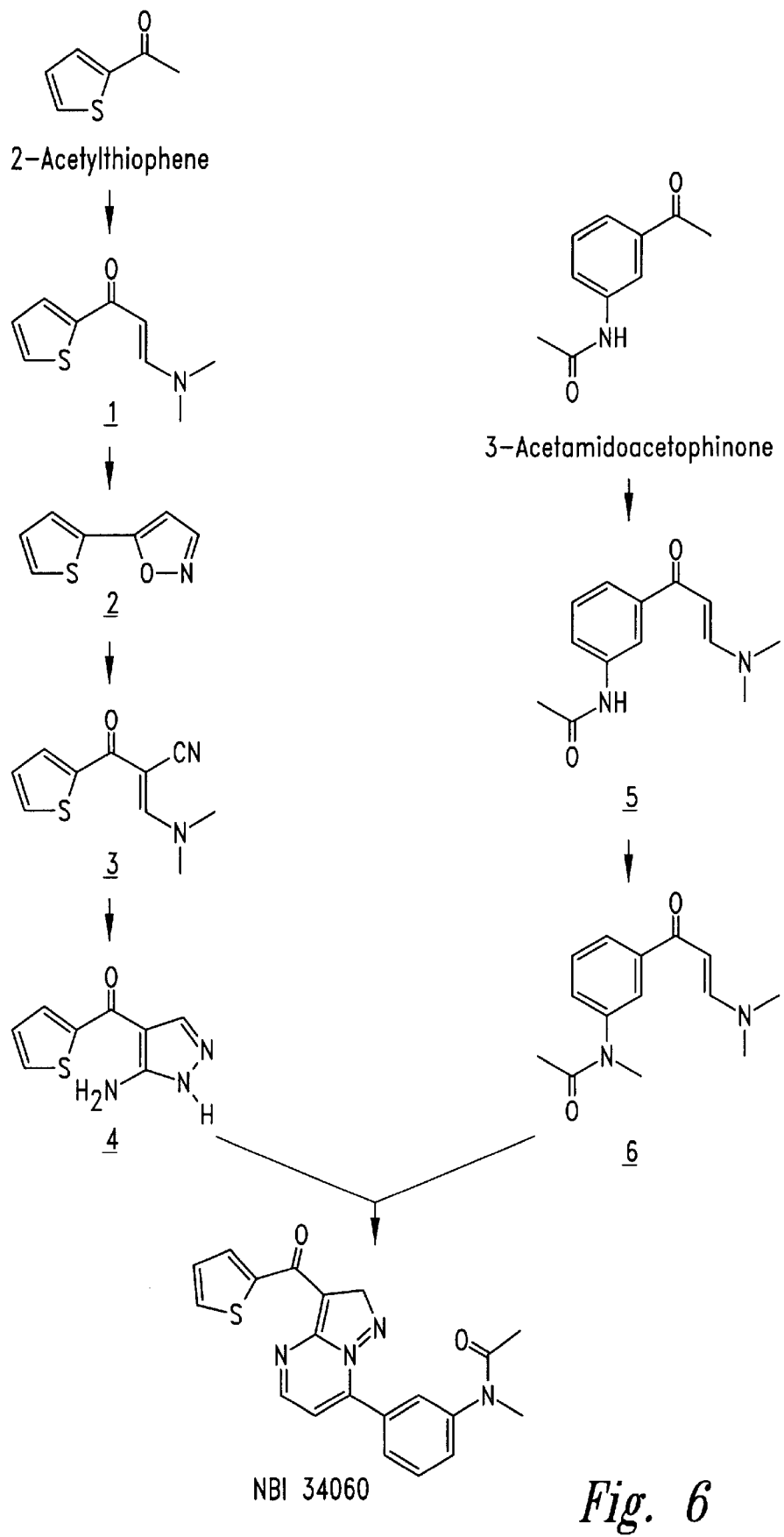
FIG. 6 represents a representative large-scale synthesis of NBI-34060.

This Example more specifically illustrates the large-scale synthesis of NBI-34060 by the convergent synthesis depicted in FIG. 6 and as summarized below.

Step 1: β-Dimethylamino-1-(2-thienyl)-2-propen-1-one

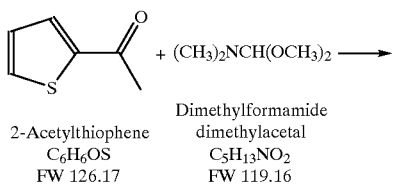

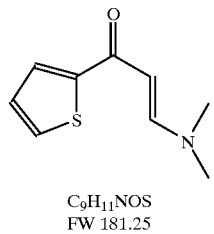

A mixture of 2-acetylthiophene (4.0 kg; Aldrich), dimethylformamide dimethylacetal (7.0 kg; Lancaster) and toluene (16 L; Mallinckrodt) is heated at reflux. As methanol forms it is removed by distillation. After heating overnight thin-layer chromatography may be used to determine whether the reaction has gone to completion. If not, the reaction may be driven to completion by the addition of a further 1.5 kg of dimethylformamide dimethylacetal with continued distillation of methanol. The reaction mixture is cooled to room temperature and the solid collected by filtration. The filter cake is washed with hexanes (6 L) and dried to give 5.171 kg of product (90% yield). The material is suitable for the next reaction by thin-layer chromatographic analysis [Hex/EtOAc (1:1); starting material $R_f$=0.65; product $R_f$=0.12].

Step 2: 5-(2-Thienyl)isoxazole

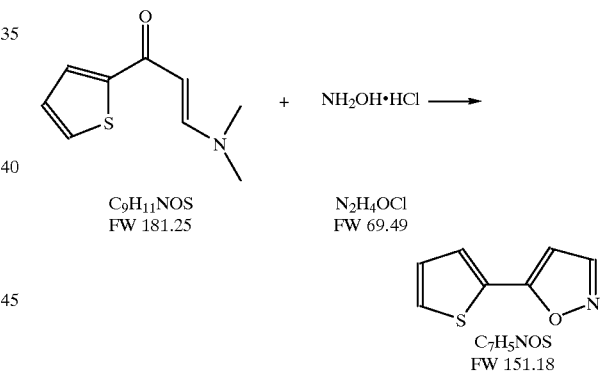

A 50 L flask is charged with β-dimethylamino-1-(2-thienyl)-2-propen-1-one (5.171 kg), hydroxylamine hydrochloride (2.0 kg; Aldrich) and methanol (20 L; Barton). The mixture is heated at reflux for 3 hours under nitrogen, at which time thin-layer chromatographic analysis may be used to verify that the reaction has gone to completion. The reaction mixture is cooled and the methanol removed on a rotary evaporator. The residue is partitioned between water (10 L) and dichloromethane (10 L; Spectrum). The organic layer is isolated and dried over sodium sulfate. The sodium sulfate is removed by filtration and the solution is concentrated under reduced pressure to yield the product as a dark yellow oil (4.313 kg, 98% yield). The material appears as a single spot on TLC [hex/EtOAc (1:1); starting material $R_f$=0.12; product $R_f$=0.63 ].

Step 3: α-[(Dimethylamino)methylene]-β-oxo-2-thiophenepropanenitrile

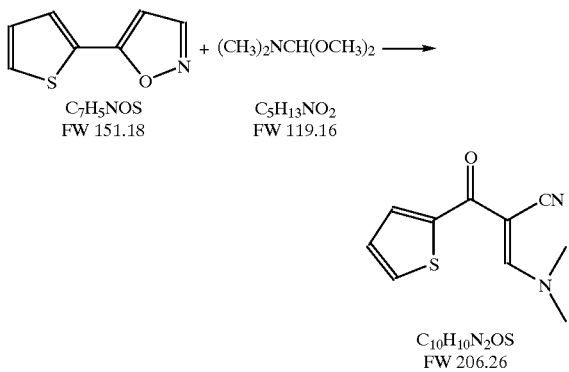

A mixture of 5-(2-thienyl)isoxazole (4.3 kg) and dimethylformamide dimethylacetal (6.1 kg; Lancaster) in toluene (12 L; Barton) is heated at reflux. As methanol forms it is removed by distillation. Solid forms from the reaction mixture. The reaction mixture is cooled and diluted with methyl-t-butyl ether (8 L; Van Waters). The precipitate is collected by filtration and washed with methyl-t-butyl ether (4 L). The solid is slurried with acetone (10 L; Batron) and hexanes (10 L; Mallinckrodt), then filtered and washed with hexanes (4 L). After drying in vacuo there is obtained 5.124 kg of α-[(dimethylamino)methylene]-β-oxo-2-thiophenepropane-nitrile (87% yield).

Step 4: (3-Amino-1H-pyroazol-4-yl)-2-thienylmethanone

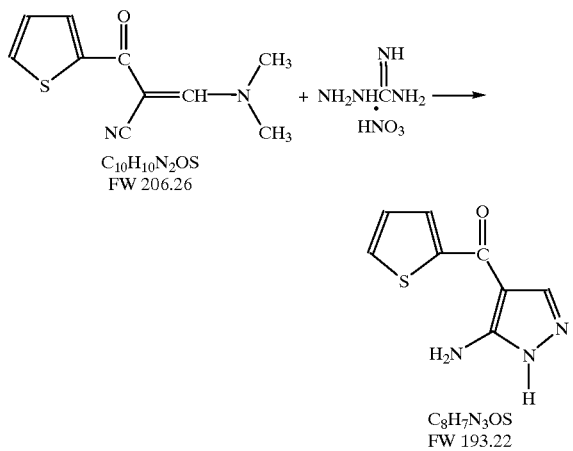

To a reaction mixture of aminoguanidine nitrate (3.0 kg; Lancaster) and α-[(dimethylamino)-methylene]-β-oxo-2-thiophenepropanenitrile (3618 g) in ethanol (20 L; Mallinckrodt) is added an aqueous solution of 10 N sodium hydroxide (2367 ml; Van Waters). The reaction mixture is heated at reflux for 6 hours then the solvents are removed on a rotary evaporator. Water (25 L) is added to the residue and a precipitate forms. The material is collected by filtration and dried to give 1.324 kg of the desired material. The pH of the aqueous mother liquors are adjusted to 7.6 with concentrated hydrochloric acid (Mallinckrodt). A second crop of material precipitats. This material (2.155 kg) is found to have a lower purity than the first crop of product. The two crops of product are combined and slurried with 20 L of ethyl acetate/hexanes (1:1). The solid is collected and washed with 4 L of hexanes. The material is slurried washed with 15 L of dichloromethane, filtered, then washed a second time with 12 L of dichloromethane. The material is filtered and dried in vacuo at 40°C to give 2.4 kg of (3-amino-1H-pyroazol-4-yl)-2-thienylmethanone (70% yield). The product is found to be greater than 98% (area) pure by HPLC.

Step 5: N-[3-[3-(Dimethylamino)-1-oxo-2-propenyl]phenyl]acetamide

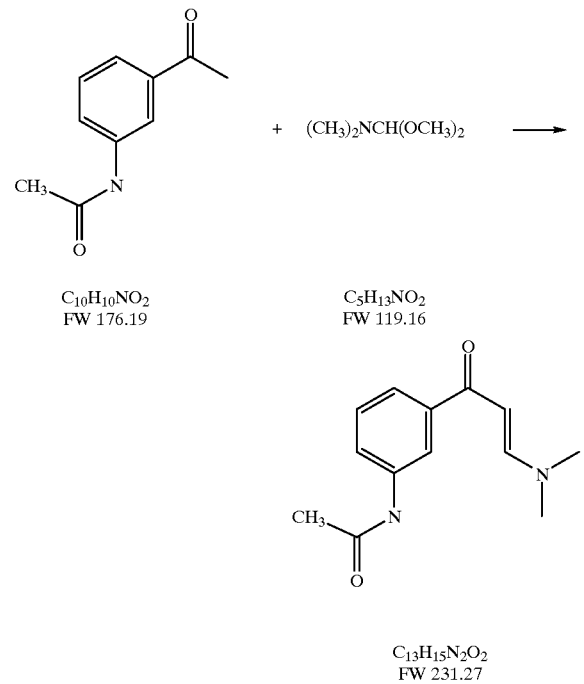

A mixture of 3-acetamidoacetophenone (3 kg; Lancaster), dimethylformamide dimethylacetal (7 L; Lancaster) and toluene (12 L; Mallinckrodt) is heated at reflux and methanol collected as it is formed. The mixture is heated overnight and a precipitate forms during this time. The reaction may be monitored by TLC analysis (EtOAc: starting material $R_f$=0.46; product $R_f$=0.10) to ensure it goes to completion. The reaction mixture is cooled and the solid is collected by filtration. The cake is washed with hexanes (4 L) then dried to give 3.77 kg (95% yield) of a light yellow powder.

Step 6: N-[3-[3-(Dimethylamino)-1-oxo-2-propenyl]phenyl]-N-methylacetamide

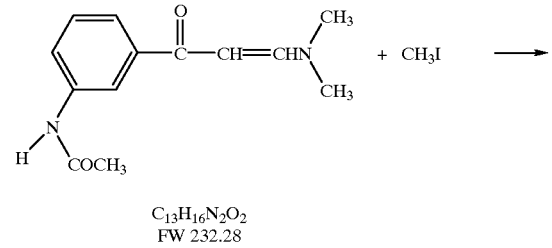

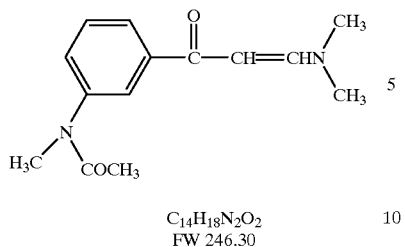

C₁₄H₁₈N₂O₂
FW 246.30

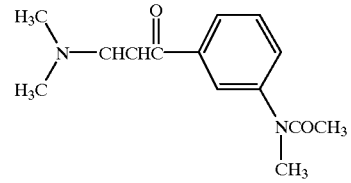

C₁₄H₁₈N₂O₂
FW 246.30

N-[3-[3-(Dimethylamino)-1-oxo-2-propenyl]phenyl] acetamide (3.77 kg) is suspended in dimethylformamide (20 L; Van Waters) and the mixture chilled in an ice bath. Sodium hydride (808 g, 60% dispersion; Aldrich) is added to the suspension under a nitrogen atmosphere. The temperature of the reaction mixture is maintained below 10?C. during the addition of the hydride. After the addition is complete the mixture is stirred for 1 hour, then methyl iodide (2.46 kg) is added slowly while maintaining the temperature below 10?C. The reaction mixture is stirred overnight and allowed to come to room temperature. HPLC analysis of the reaction mixture shows 97.7% product and ~2.3% of the starting material. The addition of methyl iodide (53 g; Aldrich) and continued stirring (5 hours) does not change this ratio. The reaction mixture is quenched by the addition of 1 L of water. The mixture is triturated with hexanes (2×4 L) which are discarded. Most of the DMF is removed under reduced pressure. The residue is diluted with water (6 L) and product is extracted with methylene chloride (20 L; Barton). The solution is dried over sodium sulfate, filtered and the solvent evaporated to give a solid. This material is triturated with hexanes (15 L) and ethyl acetate (15 L). The slurry was cooled to room temperature, filtered and washed with hexanes (0.5 L). This material is found to be only ~91% product by HPLC (area %). The material is purified by column chromatography. The material is dissolved in methylene chloride and passed through a pad of silica (~18 kg). The polarity of the eluant is gradually increased by adding ethyl acetate (Barton). Eventually the column is flushed with ethyl acetate. In this manner 2.4 kg of N-[3-[3-(Dimethylamino)-1-oxo-2-propenyl]phenyl]-N-methylacetamide is obtained with a purity of 98.05% by HPLC (area %).

Step 7: N-Methyl-N-[3-[3-(2-thienylcarbonyl)-pyrazolo[1,5-a]pyrimidin-7-yl]phenyl]acetamide

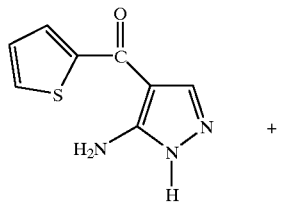 +

C₈H₇N₃OS
FW 193.22

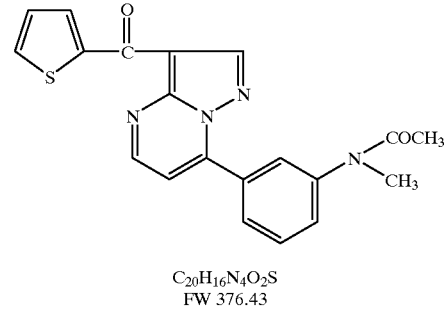

C₂₀H₁₆N₄O₂S
FW 376.43

A fifty liter flask is charged with 1.936 kg of (3-amino-1H-pyrazol-4-yl)-2-thienylmethanone, 2.450 kg of N-[3-[3-(dimethylamino)-1-oxo-2-propenyl]phenyl]-N-methylacetamide and 33.3 kg of acetic acid (Van Waters). The reaction mixture is heated at reflux for 6 hours. The reaction mixture is evaporated to a residue under reduced pressure while maintaining the temperature at approximately 45?C. The residue is dissolved in methylene chloride (8 L; Spectrum) then precipitated by the addition of 32 L of methyl-t-butyl ether. The solid is isolated by filtration and the cake washed with a small portion (3.6 L) of methyl-t-butyl ether (Van Waters). The solid is suspended in a mixture of hexanes (20 L) and ethyl acetate (20 L) and heated at reflux for 5 minutes. The mixture was allowed to cool to room temperature and the solid is isolated by filtration. The cake is washed with a small portion (6 L) of hexanes/ethyl acetate (1:1). The material is dissolved in hot methylene chloride (17 L) then the product is precipitated by the addition of hexanes (17 L). The mixture was allowed to cool to room temperature and the solid is collected by filtration. The solid may be further purified by crystallization from any one of a variety of known solvents and/or washing techniques.

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

We claim:

1. A controlled-release formulation, comprising:
   (a) a sedative-hypnotic compound or precursor thereof that is metabolized to generate a sedative-hypnotic compound in vivo, wherein the compound has a mean plasma half life ranging from 0.1 to 2 hours; and
   (b) at least one release retardant such that, following administration of the formulation to a patient, the patient has in the following order:
      (i) a time to a first maximum plasma concentration (Tmax₁) of the sedative-hypnotic compound ranging from 0.1 to 2 hours following administration;
      (ii) a time to a minimum plasma concentration (Tmin) of the sedative-hypnotic compound ranging from 2 to 4 hours, wherein the plasma concentration of the sedative-hypnotic compound at Tmin is less than 80% of the plasma concentration at $Tmax_1$;

(iii) a time to a second maximum plasma concentration ($Tmax_2$) of the sedative-hypnotic ranging from 3 to 5 hours following administration, wherein the plasma concentration of the sedative-hypnotic compound at $Tmax_2$ is from 80% to 150% of the plasma concentration at $Tmax_1$;

(iv) a plasma concentration of the sedative-hypnotic compound at 6 hours following administration of at least 20% of the plasma concentration at $Tmax_2$; and (v) a plasma concentration of the sedative-hypnotic compound at 8 hours following administration of no more than 20% of the plasma concentration at $Tmax_2$.

2. The controlled release formulation of claim 1 wherein $Tmax_1$, ranges from 0.25 to 1 hours.

3. The controlled release formulation of claim 1 wherein $Tmax_1$ is about 1 hour.

4. The controlled release formulation of claim 1 wherein the plasma concentration at Tmin is less than 70% the plasma concentration at $Tmax_1$.

5. The controlled release formulation of claim 1 wherein the plasma concentration at Tmin is less than 60% the plasma concentration at $Tmax_1$.

6. The controlled release formulation of claim 1 wherein the plasma concentration at Tmin is less than 50% the plasma concentration at $Tmax_1$.

7. The controlled release formulation of claim 1 wherein the plasma concentration at Tmin is less than 40% the plasma concentration at $Tmax_1$.

8. The controlled release formulation of claim 1 wherein Tmin is from about 2.5 to 3.5 hours.

9. The controlled release formulation of claim 1 wherein Tmin is about 3 hours.

10. The controlled release formulation of claim 1 wherein the plasma concentration at $Tmax_2$ is in the range of 90% to 140% of the plasma concentration at $Tmax_1$.

11. The controlled release formulation of claim 1 wherein the plasma concentration at $Tmax_2$ is in the range of 100% to 130% of the plasma concentration at $Tmax_1$.

12. The controlled release formulation of claim 1 wherein $Tmax_2$ ranges from 4 to 5 hours.

13. The controlled release formulation of claim 1 wherein $Tmax_2$ is about 4 hours.

14. The controlled release formulation of claim 1 wherein, at 6 hours after administration, the plasma concentration of the sedative-hypnotic compound is in excess of 30% of the plasma concentration at $Tmax_2$.

15. The controlled release formulation of claim 1 wherein, at 6 hours after administration, the plasma concentration of the sedative-hypnotic compound is in excess of 40% of the plasma concentration at $Tmax_2$.

16. The controlled release formulation of claim 1 wherein, at 8 hours after administration, the plasma concentration of the sedative-hypnotic compound is less than 15% of the plasma concentration at $Tmax_2$.

17. The controlled release formulation according to claim 1 wherein the sedative-hypnotic compound is NBI-34060.

18. The controlled release formulation of claim 17 wherein the plasma concentration of NBI-34060 at $Tmax_1$ is in excess of 5 ng/mL.

19. The controlled release formulation of claim 17 wherein the plasma concentration of NBI-34060 at $Tmax_1$ is in the range of 5 ng/mL to 20 ng/mL.

20. The controlled release formulation of claim 17 wherein the plasma concentration of NBI-34060 at $Tmax_1$ is in the range of 7.5 to 15 ng/mL.

21. The controlled release formulation of claim 17 wherein the plasma concentration of NBI-34060 at $Tmax_1$ is in the range of 10 to 13 ng/mL.

22. The controlled release formulation of claim 1 wherein the plasma concentration of NBI-34060 at Tmin is in excess of 3 ng/mL.

23. The controlled release formulation of claim 1 wherein the plasma concentration of NBI-34060 at Tmin is in excess of 4 ng/mL.

24. The controlled release formulation of claim 1 wherein the plasma concentration of NBI-34060 at Tmin is in excess of 5 ng/mL.

25. The controlled release formulation of claim 1 wherein the sedative-hypnotic compound is zaleplon.

26. The controlled release formulation of claim 1 wherein at least one release retardant is selected from the group consisting of hydroxypropylmethyl cellulose, ethyl cellulose, poly(ethylacrylate methylmethacrylate), methacrylic acid copolymer (Type A, Type B, Type C), hydroxypropyl cellulose, carbomer, polyethylene glycol, polyvinylpyrrolidone, gelatin, corn starch, stearyl alcohol, carnuba wax, white wax, glyceryl monostearate, glyceryl distearate, guar gum, xanthan gum and chitosan.

27. The controlled release formulation of claim 1 wherein the formulation comprises a first immediate release (IR) unit that yields $Tmax_1$ from 0.1 to 2 hours following administration; and a second IR unit with a delayed release that yields $Tmax_2$ from 3 to 5 hours following administration.

28. The controlled release formulation according to claim 27 in the form of a pellet.

29. A method for promoting sleep in a mammal, comprising administering to the mammal an effective amount of the controlled-release formulation of claim 1.

30. A method for reducing anxiety in a mammal, comprising administering to the mammal an effective amount of the controlled-release formulation of claim 1.

31. A method for inhibiting convulsions in a mammal, comprising administering to the mammal an effective amount of the controlled-release formulation of claim 1.

32. The method according to any one of claims 29, 30 or 31 wherein the sedative-hypnotic compound is NBI-34060.

33. The method according to any one of claims 29, 30 or 31 wherein the sedative-hypnotic compound is zaleplon.

34. The method according to any one of claims 29, 30 or 31 wherein the sedative-hypnotic compound is zaleplone.

35. The controlled release formulation of claim 1 wherein, at 8 hours after administration, the plasma concentration of the sedative-hypnotic compound is no more than 15% of the plasma concentration at $Tmax_2$.

* * * * *

UNITED STATES PATENT AND TRADEMARK OFFICE
CERTIFICATE OF CORRECTION

PATENT NO.     : 6,485,746 B1
DATED          : November 26, 2002
INVENTOR(S)    : D. Bruce Campbell et al.

It is certified that error appears in the above-identified patent and that said Letters Patent is hereby corrected as shown below:

<u>Column 26,</u>
Lines 53 and 54, "The method according to any one of claims 29, 30 or 31 wherein the sedative-hypnotic compound is zaleplone." Should be corrected to read as -- The method according to any one of claims 29, 30 or 31 wherein the formulation is administered orally in the form of a tablet. --

Signed and Sealed this

Tenth Day of June, 2003

JAMES E. ROGAN
*Director of the United States Patent and Trademark Office*